United States Patent [19]
Boyd et al.

[11] Patent Number: 5,401,851
[45] Date of Patent: Mar. 28, 1995

[54] ANGIOTENSIN II ANTAGONISTS

[75] Inventors: Donald B. Boyd, Greenwood; Kenneth L. Hauser, Greencastle; Sherryl L. Lifer, Indianapolis; Winston S. Marshall, Bargersville; Alan D. Palkowitz; William Pfeifer, both of Indianapolis; Jon K. Reel, Carmel; Richard L. Simon, Greenwood; Mitchell I. Steinberg, Indianapolis; Kumiko Takeuchi, Indianapolis; K. Jeff Thrasher, Indianapolis; Celia A. Whitesitt, Greenwood, all of Ind.

[73] Assignee: Eli Lilly and Company, Indianapolis, Ind.

[21] Appl. No.: 49,917

[22] Filed: Apr. 20, 1993

Related U.S. Application Data

[63] Continuation-in-part of Ser. No. 892,867, Jun. 3, 1992, abandoned.

[51] Int. Cl.⁶ .................. A61K 31/415; A61K 31/44; A61K 31/505; C07D 233/58; C07D 239/26; C07D 213/06
[52] U.S. Cl. .................................. 548/112; 548/250; 548/252; 548/253; 548/254; 548/313.1; 548/314.7; 548/312.1; 548/326.5; 548/950; 548/333.5; 548/953; 548/324.1; 548/338.1; 546/22; 546/275; 546/276; 546/278; 544/243; 544/298; 544/333
[58] Field of Search ............... 548/336, 337, 341, 342, 548/346, 318, 250, 252, 253, 254, 112, 950, 953; 546/22, 275, 276, 278; 544/243, 298, 333; 514/392, 397, 398, 399, 400, 381, 340, 341, 343

[56] References Cited

U.S. PATENT DOCUMENTS 3,772,315 11/1973 Regel et al. .................. 260/296 R
3,872,121 3/1975 Kummer et al. ............... 548/314.7
4,089,962 5/1978 Harrison et al. .................. 424/269

(List continued on next page.)

FOREIGN PATENT DOCUMENTS 24829   3/1981  European Pat. Off. .
0058047 8/1982  European Pat. Off. ............ 548/336
58047   8/1982  European Pat. Off. .
0072615 2/1983  European Pat. Off. ............ 548/341
125033  11/1984 European Pat. Off. .
253310  1/1988  European Pat. Off. .
323841  7/1989  European Pat. Off. .
324377  7/1989  European Pat. Off. .
429257  11/1990 European Pat. Off. .

OTHER PUBLICATIONS

Wong, et al., *J. Pharm. Exptl. Ther.*, 247 (1), 1 (1988).
Danishefsky, et al., *J. Org. Chem.*, 42 (10) 1821–1823 (1977).
CA115:256180f Preparation . . . antagonists. Lifer et al., p. 867, 1991.
CA116:48795d Inidazole . . . material. Hirabayashi et al., p. 512, 1992.
CA117:181628p Polymeric . . . material. Yamanouchi, p. 694, 1992.
CA117:233975w Synthesis . . . —furanones. Kaiser (1992).

*Primary Examiner*—Mary C. Lee
*Assistant Examiner*—Joseph McKane
*Attorney, Agent, or Firm*—Steven P. Caltrider; David E. Boone

[57] ABSTRACT

This invention provides novel phenyl and heterocyclic derivatives, their pharmaceutical formulations and their methods of use for antagonizing angiotensin II receptors in mammals.

8 Claims, No Drawings

U.S. PATENT DOCUMENTS

| | | | |
|---|---|---|---|
| 4,207,324 | 6/1980 | Matsumura et al. | 424/273 R |
| 4,226,878 | 10/1980 | Iizuka et al. | 424/273 R |
| 4,299,769 | 11/1981 | McEvoy et al. | 548/314.7 |
| 4,340,598 | 7/1982 | Furukawa et al. | 424/273 R |
| 4,355,040 | 10/1982 | Furukawa et al. | 424/273 B |
| 4,379,927 | 4/1983 | Vorbrüggen et al. | 544/139 |
| 4,448,781 | 5/1984 | Cross et al. | 424/269 |
| 4,528,195 | 7/1985 | Thorogood | 514/396 |
| 4,582,847 | 4/1986 | Furukawa et al. | 514/400 |
| 4,584,383 | 4/1986 | Pharhi | 546/278 |
| 4,880,804 | 11/1989 | Carini et al. | 514/234 |
| 4,908,363 | 3/1990 | Klotzer et al. | 514/235.8 |
| 4,916,129 | 4/1990 | Carini et al. | 514/235.2 |
| 4,962,120 | 10/1990 | Bailey et al. | 514/399 |
| 5,053,329 | 10/1991 | Chen et al. | 435/119 |
| 5,064,825 | 11/1991 | Chakravarty et al. | 514/221 |
| 5,073,566 | 12/1991 | Lifer et al. | 514/381 |
| 5,102,880 | 4/1992 | Chakravarty et al. | 514/212 |
| 5,102,903 | 4/1992 | Smith | 514/406 |
| 5,173,494 | 12/1992 | Chiu et al. | 514/303 |
| 5,175,164 | 12/1992 | Bagley et al. | 514/259 |
| 5,177,074 | 1/1993 | Allen et al. | 514/234.2 |
| 5,180,724 | 1/1993 | Bowles et al. | 514/248 |
| 5,183,810 | 2/1993 | Greenlee et al. | 514/63 |
| 5,210,211 | 5/1993 | Hodges et al. | 548/314.7 |

ANGIOTENSIN II ANTAGONISTS

This application is a continuation in part of Thrasher et al., U.S. Ser. No. 07/892,867, filed Jun. 3, 1992, now abandoned.

BACKGROUND OF THE INVENTION

The hormone angiotensin II is recognized as one of the most potent vasopressor agents that produces hypertension in mammals. The action of the enzyme renin on the plasma protein substrate angiotensinogen results in the production of an inactive decapeptide, angiotensin I, which upon conversion by the nonselective selective angiotensin converting enzyme (ACE) provides angiotensin II, the active hormone. See, e.g., Regoli et al., *Pharm, Rev.*, 26, 69 (1974).

Angiotensin II causes vasoconstriction and stimulates aldosterone secretion (from the adrenal gland) that results in a rise of both blood volume and pressure. Inhibitors of angiotensin II are therefore useful in treating hypertension, congestive heart failure, renal insufficiency associated with diabetic or hypertensive nephropathy, and glaucoma. See Garrison et al., in The Pharmacological Basis of Therapeutics, 8th Edition, Eds. A. G. Gilman, E. S. Goodman, T. W. Rall, A. S. Nies, and P. Taylor, Pergamon Press, New York, 1990: p. 761-762; and Dzau V. J., *The New Eng. J. Med.* 924: 1124-1130 (1991).

Angiotensin II also can act on other organs such as the brain (Fitzsimmons, *Rev, Physiol, Biochem. Pharmacol.*, 87, 117, (1980)). Antagonists of angiotensin II are therefore useful in enhancing cognitive performance in patients affected by conditions such as age associated mental impairment or Alzheimer's disease and in treating cognitive disorders such as anxiety. See Dennes et al. *Brit. J. Pharmacol.* 105: 88p (April 1992); and Barnes, J. M., et al. *FASEB J.* 5: 678 (March 1991).

In addition, angiotensin II acts on a variety of glandular tissues including the kidney, liver, and ovaries. Antagonists of angiotensin II are useful in treating conditions, disorders, or diseases of these tissues associated with excessive or unregulated angiotensin II activity. Antagonists of angiotensin II are also useful in treating kidney damage due to nonsteroidal antiinflammatory agents.

Angiotensin II has a role in regulation of the rate of cell growth and differentiation. Inhibitors of angiotensin II are therefore useful in treating disorders marked by excessive cell proliferation such as restenosis. See, e.g., Naftilan et al., *J. Clin. Invest,* 83, 1419 (1989), Kauffman et al., *Life Sciences,* 49:223-228 (1991), and Jackson et al., *Nature,* 335, 437 (1988).

Some antihypertensive agents act as inhibitors of ACE thus blocking the formation of angiotensin II and its resulting increase of blood pressure. More recently, both peptide and nonpeptide receptor antagonists of angiotensin II have been disclosed-see, e.g., EPO Patent Application Publication 253310 and references contained therein, and Chiu et al., *J. Pharmacol, Exp. Ther.,* 250, 867 (1989). Although these compounds and others have had an important role in uncovering the physiological roles for Angiotensin II, their therapeutic usefulness was ultimately limited by either partial agonist activity, metabolic instability or both. See Ashworth R. W. *Birkhauser Verlag* 26 (1982).

The present invention provides novel, potent, and effective compounds that antagonize angiotensin II at receptor sites in the body and are therefore useful in treating conditions associated with excessive or unregulated angiotensin II activity such as hypertension, congestive heart failure, cognitive disorders, renal insufficiency associated with diabetic or hypertensive nephropathy, glaucoma, kidney damage due to nonsteroidal antiinflammatory agents, and restenosis.

SUMMARY OF THE INVENTION

This invention provides compounds of Formula I

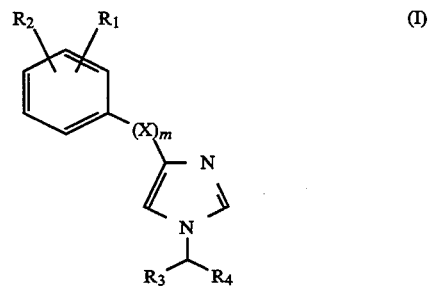

and pharmaceutically acceptable salts or solvates thereof wherein:

$R_1$ is $CO_2H$, $SO_3H$, $PO_3H_2$, $CONHSO_2R_5$ or 5-tetrazolyl;

$R_2$ is H, —OH, —OCOCH$_3$, halo, $C_1$-$C_4$ alkyl, amino, acetamido, or $C_1$-$C_4$ alkoxy;

X is —(CH$_2$)$_m$NHCO—, —(CH$_2$)$_m$CONH—, —O—, —NH—, —CH$_2$—, —(CH$_2$)$_m$CO—, or —CO(CH$_2$)$_m$—;

$R_3$ is $C_4$-$C_9$ straight chain alkyl, $C_4$-$C_9$ straight chain trifluoroalkyl, $C_4$-$C_9$ straight chain alkenyl, or $C_4$-$C_9$ straight chain trifluoroalkenyl;

$R_4$ is —CONH($C_1$-$C_4$ alkyl), —CONH($C_1$-$C_4$ trifluoroalkyl), —CONH (hydroxy-$C_1$-$C_4$ alkyl),

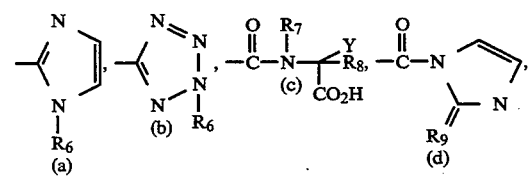

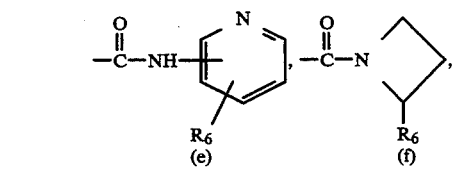

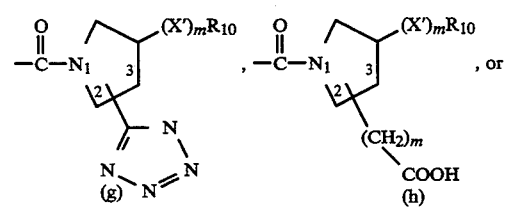

-continued

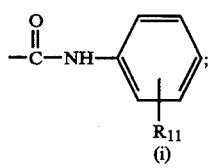
(i)

$R_5$ is phenyl, $C_1$–$C_4$ alkyl substituted phenyl, $C_1$–$C_5$ alkyl, or $C_1$–$C_5$ trifluoroalkyl;

$R_6$ is $(CH_2)_p R_1$, or $C_1$–$C_4$ alkyl;

$R_7$ is H or $CH_3$;

$R_8$ is H or $-(CH_2)_q R_{12}$;

$R_9$ is O or S;

$R_{10}$ is H, $-(CH_2)_p R_1$, $C_1$–$C_7$ alkyl, $C_1$–$C_7$ trifluoroalkyl, halo, substituted or unsubstituted phenyl, 3-pyridyl, 2-pyrimidyl, furanyl, oxazolyl, isoxazolyl, a substituted or unsubstituted fused bicyclic, a substituted or unsubstituted fused tricyclic, or when m is 0, 4,4-ethylenedioxy;

$R_{11}$ is H, OH, $C_1$–$C_4$ alkoxy, $CO_2H$, $SO_3H$, $PO_3H_2$, $CONHSO_2R_5$, or tetrazolyl;

$R_{12}$ is OH, $NH_2$, or $CO_2H$;

Y is a R group of a naturally occurring amino acid;

X' is $-O-$, $-(CH_2)_p-$, or $-S-$;

m is independently 0 or 1;

p is independently 0, 1, 2, 3 or 4; and q is 1, 2, 3, or 4;

providing that when $R_4$ is (g) or (h), and $R_{10}$ is not H, the carboxy of (h) or tetrazolyl of (g) is in position 2; and when $R_4$ is (g) or (h), m is 0, and $R_{10}$ is H, the carboxy of (g) or tetrazolyl of (h) is in position 2 or 3; and a pharmaceutically acceptable salt or solvate thereof.

This invention also provides a method for treating hypertension which comprises administering to a mammal in of such treatment an antihypertensive amount of a compound of the Formula I.

This invention further provides methods for treating congestive heart failure, renal insufficiency associated with hypertensive or diabetic nephropathy, restenosis, kidney damage due to nonsteroidal antiinflammatory agents, anxiety, and glaucoma which comprise administering to a mammal in need of treatment a pharmaceutically effective amount of a compound of the Formula I.

A further aspect of the present invention is a method of enhancing cognitive performance which comprises administering to a mammal in need of enhancement a pharmaceutically effective amount of a compound of the Formula I.

Also provided are pharmaceutical formulations comprising a compound of Formula I together with one or more pharmaceutically acceptable excipients, carriers, or diluents.

An additional aspect of this invention is a process of preparing the preferred stereoisomer of Formula I, comprising:

coupling a compound of the formula (XXI)

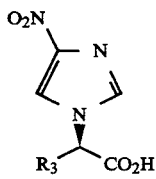
(XXI)

wherein $R_3$ is $C_4$–$C_9$ straight chain alkyl, $C_4$–$C_9$ straight chain trifluoroalkyl, $C_4$–$C_9$ straight chain alkenyl, or $C_4$–$C_9$ straight chain trifluoroalkenyl; to a compound of the formula:

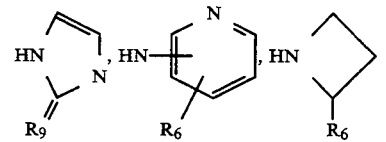

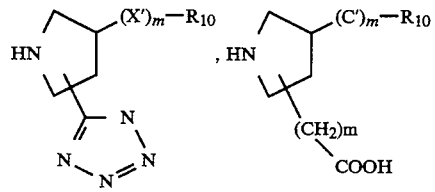

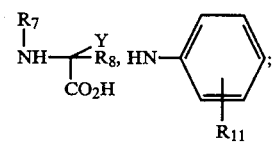

wherein $R_6$, $R_7$, $R_8$, $R_9$, $R_{10}$, $R_{11}$, $R_{12}$, and Y are the same as previously defined;

reducing the nitro of the compound of the formula (XXI) to produce an amino imidazole;

coupling the amino imidazole to a compound of the formula:

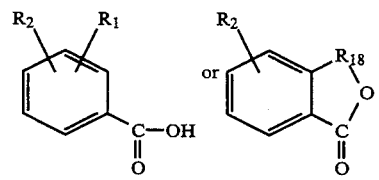

wherein $R_2$ and $R_1$ are the same as previously defined; $R_{18}$ is $SO_2$ or $C=O$.

DETAILED DESCRIPTION AND PREFERRED EMBODIMENT

As noted above, the invention provides compounds of the Formula I which antagonize angiotensin II at the receptor sites in the body. The preferred compounds of this invention are those of Formula I wherein:

$R_4$ is

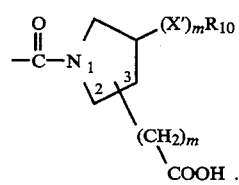
(h)

Particularly preferred compounds of this invention are those of Formula Ia:

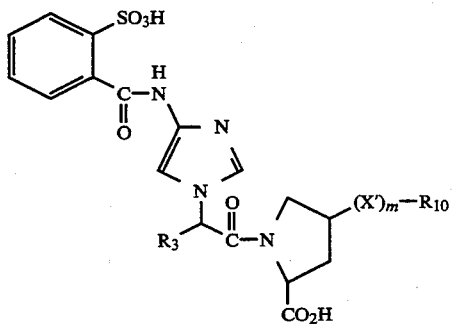
(Ia)

wherein R$_3$ is a C$_4$–C$_9$ straight chain alkyl; R$_{10}$ is an unsubstituted or para substituted phenyl, a substituted or unsubstituted fused bicyclic, a substituted or unsubstituted fused tricyclic; m is 0 or 1; X' is —O—, —S—, or (CH$_2$)$_p$; and p is 0, 1, 2, 3 or 4.

Most preferred compounds are compounds in which X' is —O—, and R$_{10}$ is a substituted phenyl of the formula:

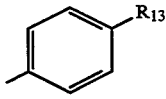

wherein R$_{13}$ is —(CH$_2$)$_p$R$_1$, —O(CH$_2$)$_p$R$_1$, —SO$_2$NR$_{14}$R$_{15}$, —(CH$_2$)$_p$CONR$_{14}$R$_{15}$, —(CH$_2$)$_p$NR$_{16}$SO$_2$(C$_1$–C$_4$ alkyl or C$_1$–C$_4$ trifluoroalkyl), or a heteroaryl selected from imidazolyl, triazolyl, tetrazolyl, thioazolyl, isoxazolyl, or oxazolyl, said heteroaryl being optionally substituted with —(CH$_2$)$_p$R$_1$; R$_{14}$ and R$_{15}$ are independently H, C$_1$–C$_4$ alkyl, —(CH$_2$)$_p$CO$_2$H or taken together with nitrogen to which they are bonded constitute a heterocylic ring selected from the groups consisting of pyrrolidino or piperidino, said heterocyclic ring being optionally substituted with —COOH; R$_{16}$ is H or C$_1$–C$_4$ alkyl.

Examples of the preferred compounds include the following:

1-[1-oxo-2-[4-(2-sulfobenzoyl)amino-1H-imidazol-1-yl]octyl]-4-cis-(4-carboxyphenoxy)-L-proline
1-[1-oxo-2-[4-(2-sulfobenzoyl)amino-1H-imidazol-1-yl]octyl]-4-cis-(4-carboxymethylphenoxy)-L-proline
1-[1-oxo-2-[4-(2-sulfobenzoyl)amino-1H-imidazol-1-yl]octyl]-4-cis- (4-t-butyloxyphenoxy)-L-proline
1-[1-oxo-2-[4-(2-sulfobenzoyl)amino-1H-imidazol-1-yl]octyl]-4-cis-(4-methylsulfonylphenoxy)-L-proline
1-[1-oxo-2-[4-(2-sulfobenzoyl)amino-1H-imidazol-1-yl]octyl]-4-cis-(5-benzofuranoxy)-L-proline
1-[1-oxo-2-[4-(2 -sulfobenzoyl)amino-1H-imidazol-1-yl]octyl]-4-cis-(2-naphthoxy)-L-proline
1-[1-oxo-2-[4-(2-sulfobenzoyl)amino-1H-imidazol-1-yl]octyl]-4-cis-(4-carboxymethoxyphenoxy)-L-proline
1-[1-oxo-2-[4-(2-sulfobenzoyl)amino-1H-imidazol-1-yl]octyl]-4-cis-(2-carboxybenzofuran-5-yloxy)-L-proline
1-[1-oxo-2-[4-(2-sulfobenzoyl)amino-1H-imidazol-1-yl]octyl]-4-cis-((4-methylene phosphonic acid)-phenoxy)-L-proline The terms "C$_1$–C$_4$ alkyl," "C$_1$–C$_5$ alkyl," "C$_1$–C$_7$ alkyl," and "C$_1$–C$_9$ alkyl" represent a cyclo, straight or branched chain alkyl group having from one to four, five, seven or nine carbon atoms respectively such as methyl, ethyl, n-propyl, isopropyl, n-butyl, isobutyl, sec-butyl, t-butyl, pentyl, isopentyl, 1-methylbutyl, 1-ethylpropyl, neopentyl, tert-pentyl, cyclopentyl, n-hexyl, isohexyl, 4-methyl hexyl, cyclohexyl, cyclohexyl methyl, n-heptyl, t-heptyl, iso-heptyl and the like.

The term "hydroxy-C$_1$–C$_4$ alkyl" is a C$_1$–C$_4$ alkyl substituted with a hydroxy. A hydroxy-C$_1$–C$_4$ alkyl is preferably of the formula HO(CH$_2$)$_q$—, where q is 1 to 4.

The terms "C$_1$–C$_4$ trifluoroalkyl," "C$_1$–C$_5$ trifluoroalkyl," and "C$_1$–C$_7$ trifluoroalkyl" represent a straight or branched chain alkyl group having from one to four, five or seven carbon atoms respectively in which the primary carbon is substituted with fluorine.

The term "C$_4$–C$_9$ straight chain alkyl" represents a straight chain alkyl group having from four to nine carbon atoms. Examples of a "C$_4$–C$_9$ straight chain alkyl" include n-butyl, n-pentyl, n-hexyl, n-heptyl, n-octyl, and n-nonyl.

The term "C$_4$–C$_9$ straight chain trifluoroalkyl" represents a C$_4$–C$_9$ straight chain trifluoroalkyl group in which the primary carbon is substituted with fluorine.

The terms "C$_1$–C$_4$ alkoxy" and "C$_1$–C$_7$ alkoxy" represent a C$_1$–C$_4$ or C$_1$–C$_7$ alkyl group covalently bonded to the parent moiety by an —O— linkage.

The terms "C$_1$–C$_4$ trifluoroalkoxy" and "C$_1$–C$_7$ trifluoroalkoxy" represent a straight or branched chain C$_1$–C$_4$ or C$_1$–C$_7$ trifluoroalkyl group covalently bonded to the parent moiety by an —O— linkage.

The term "C$_4$–C$_9$ straight chain alkenyl" represents a straight chain alkyl group having from four to nine carbon atoms and one double bond. Examples of a "C$_4$–C$_9$ straight chain alkenyl" include n-butenyl, n-pentenyl, n-hexenyl, n-heptenyl, n-octenyl, and n-nonenyl.

The term "C$_4$–C$_9$ straight chain trifluoroalkenyl" represents a C$_4$–C$_9$ straight chain alkenyl group in which the primary carbon atom is trisubstituted with fluorine. Examples of a "C$_4$–C$_9$ straight chain trifluoroalkenyl" include 4-trifluoro-n-2-butenyl, 5-trifluoro-n-2-pentenyl, 6-trifluoro-n-3-hexenyl, 7-trifluoro-n-4-heptenyl, 8-trifluoro-n-6-octenyl, and 9-trifluoro-n-5-nonenyl.

The term "R group of a naturally occurring amino acid" represents the variable region of the naturally occurring amino acids and is understood in the art. See, for example, Lehninger A. L. Biochemistry, 2nd edition, Worth Publishers, p. 73–75, 1975.

The term "—(CH$_2$)$_p$R$_1$" represents a straight chain alkyl, branched alkyl, or a straight chain alkenyl bonded to R$_1$ or R$_1$ when p is zero. Examples of "—(CH$_2$)$_p$R$_1$ include groups in which the straight chain alkyl, branched alkyl or straight chain alkenyl portion includes methylene, ethylene, trimethylene, tetramethylene, methylethylene, ethylethylene, 2-methyltrimethylene, ethenylene, propenylene, and butenylene.

The term "halo" includes fluoro, chloro, bromo, and iodo.

The term "substituted or unsubstituted phenyl" represents phenyl or phenyl substituted with one or more groups selected from —(CH$_2$)$_p$R$_1$, —O(CH$_2$)$_p$R$_1$, —(CF$_2$)$_p$CO$_2$H, C$_1$–C$_7$ alkyl, C$_1$–C$_7$ trifluoroalkyl, halo, —(CH$_2$)$_p$OH, cyano, phenylsulfonyl, phenyl, thiophenyl, thiocarboxy, C$_1$–C$_7$ trifluoroalkoxy, C$_1$–C$_7$ alkoxy, —S(C$_1$–C$_4$ alkyl), —SO(C$_1$–C$_9$ alkyl), —SO$_2$(-

$C_1$–$C_9$ alkyl), —$SO_2NR_{14}R_{15}$; —$(CH_2)_pCONR_{14}R_{15}$, —$(CH_2)_pNR_{16}SO_2(C_1$–$C_4$ alkyl or $C_1$–$C_4$ trifluoroalkyl), or a heteroaryl selected from imidazolyl, triazolyl, tetrazolyl, thioazolyl, isoxazolyl, or oxazolyl, said heteroaryl being optionally substituted with —$(CH_2)_pR_1$; $R_{14}$ and $R_{15}$ are independently H, $C_1$–$C_4$ alkyl, —$(CH_2)_pCO_2H$ or taken together with nitrogen to which they are bonded constitute a heterocylic ring selected from the groups consisting of pyrrolidino or piperidino, said heterocylic ring being optionally substituted with —COOH; $R_{16}$ is H or $C_1$–$C_4$ alkyl. Preferably, a substituted or unsubstituted phenyl is a phenyl substituted with one substituent, preferably —$(CH_2)_pR_1$.

The term "fused bicyclic" represents a stable fused bicyclic ring system of the formula:

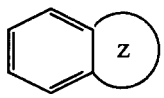

wherein Z represents a substituted or unsubstituted, saturated or unsaturated 5 or 6 membered ring, said ring having from zero to three heteroatoms that are the same or different and that are selected from the group consisting of sulfur, oxygen, and nitrogen; and when Z contains two adjacent carbon atoms, the adjacent carbon atoms may be structured to form a group of the formula —CH=CH—CH=CH—; provided that (1) when the heterocyclic ring contains 5 members, the heteroatoms comprise not more than one sulfur or two oxygen atoms but not both; (2) when the heterocyclic ring contains 6 members, sulfur and oxygen are not present; and (3) when the heterocyclic ring contains a sulfur or oxygen atom, the benzofusion is joined to a carbon adjacent to said sulfur or oxygen atom. The fused bicyclic may be attached at any carbon which affords a stable structure. The fused bicyclic may be substituted with one or two groups independently selected from —$(CH_2)_pR_1$, —$O(CH_2)_pR_1$, —$(CF_2)_pCO_2H$, $C_1$–$C_7$ alkyl, $C_1$–$C_7$ trifluoroalkyl, halo, —$(CH_2)_pOH$, cyano, phenylsulfenyl, phenyl, thiophenyl, thiocarboxy, $C_1$–$C_7$ trifluoroalkoxy, $C_1$–$C_7$ alkoxy, —$S(C_1$–$C_4$ alkyl), —$SO(C_1$–$C_9$ alkyl), —$SO_2(C_1$–$C_9$ alkyl), —$SO_2NR_{14}R_{15}$, —$(CH_2)_pCONR_{14}R_{15}$, —$(CH_2)_pNR_{16}SO_2(C_1$–$C_4$ alkyl or trifluoroalkyl), or a heteroaryl selected from imidazolyl, triazolyl, tetrazolyl, thioazolyl, isoxazolyl, or oxazolyl, said heteroaryl being optionally substituted with —$(CH_2)_pR_1$; $R_{14}$ and $R_{15}$ are independently H, $C_1$–$C_4$ alkyl, —$(CH_2)_pCO_2H$ or taken together with nitrogen to which they are bonded constitute a heterocylic ring selected from the groups consisting of pyrrolidino or piperidino, said heterocylic ring being optionally substituted with —COOH; $R_{16}$ is H or $C_1$–$C_4$ alkyl.

The term "fused tricyclic" represents a stable fused tricyclic ring system of the formula:

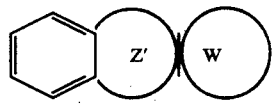

wherein Z' represents a saturated or unsaturated 5 membered ring, said ring having zero or one heteroatom that is selected from the group consisting of sulfur, oxygen, and nitrogen; W represents a substituted or unsubstituted, saturated or unsaturated 6 membered ring, said ring having from zero to three nitrogen atoms. The fused tricyclic may be attached at any carbon which affords a stable structure. The fused tricyclic may be substituted with one or two groups independently selected from —$(CH_2)_pR_1$, —$O(CH_2)_pR_1$, —$(CF_2)_pCO_2H$, $C_1$–$C_7$ alkyl, $C_1$–$C_7$ trifluoroalkyl, halo, —$(CH_2)_pOH$, cyano, phenylsulfenyl, phenyl, thiophenyl, thiocarboxy, $C_1$–$C_7$ trifluoroalkoxy, $C_1$–$C_7$ alkoxy, —$S(C_1$–$C_4$ alkyl), —$SO(C_1$–$C_9$ alkyl), —$SO_2(C_1$–$C_9$ alkyl), —$SO_2NR_{14}R_{15}$, —$(CH_2)_pCONR_{14}R_{15}$, —$(CH_2)_pNR_{16}SO_2(C_1$–$C_4$ alkyl or trifluoroalkyl), or a heteroaryl selected from imidazolyl, triazolyl, tetrazolyl, thioazolyl, isoxazolyl, or oxazolyl, said heteroaryl being optionally substituted with —$(CH_2)_pR_1$; $R_{14}$ and $R_{15}$ are independently H, $C_1$–$C_4$ alkyl, —$(CH_2)_pCO_2H$ or taken together with nitrogen to which they are bonded constitute a heterocylic ring selected from the groups consisting of pyrrolidino or piperidino, said heterocylic ring being optionally substituted with —COOH; $R_{16}$ is H or $C_1$–$C_4$ alkyl.

The term "$C_1$–$C_4$ alkyl substituted phenyl" represents a phenyl substituted in any position with a $C_1$–$C_4$ alkyl as previously defined.

The term "carboxy protecting group" as used in the specification refers to one of the ester derivatives of the carboxylic acid group commonly employed to block or protect the carboxylic acid group while reactions are carried out on other functional groups on the compound. The species of carboxy-protecting group employed is not critical so long as the derivatized carboxylic acid is stable to the condition of subsequent reaction(s) and can be removed at the appropriate point without disrupting the remainder of the molecule. See E. Haslam, *Protective Groups in Organic Chemistry*, J. G. W. McOmie, Ed., Plenum Press, New York, N.Y., 1973, Chapter 5, and T. W. Greene, *Protective Groups in Organic Synthesis*, John Wiley and Sons, New York, N.Y., 1981, Chapter 5. A related term is "protected carboxy," which refers to a carboxy-protecting groups.

The term "amino protecting group" as used in the specification refers to substituents of the amino group commonly employed to block or protect the amino functionality while reacting other functional groups on the compound. The species of amino-protecting group employed is not critical so long as the derivatized amino group is stable to the condition of subsequent reaction(s) and can be removed at the appropriate point without disrupting the remainder of the molecule. Preferred amino-protecting groups are t-butoxycarbonyl and the benzyloxycarbonyl. See J. W. Barton, *Protective Groups in Organic Chemistry*, J. G. W. McOmie, Ed., Plenum Press, New York, N.Y., 1973, Chapter 2, and T. W. Greene, *Protective Groups in Organic Synthesis*, John Wiley and Sons, New York, N.Y., 1981, Chapter 7. The related term "protected amino" defines an amino group substituted with an amino protecting group as previously discussed.

By virtue of their acidic moieties, the compounds of Formula I include the pharmaceutically acceptable base addition salts thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine ethanolamine and the like. The potassium and sodium salt forms are particularly preferred.

Because of the heterocycle moiety, the compounds of Formula I can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para toluenesulfonic, methanesulfonic, oxalic, para bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, 2-butyne-1,4 dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, B-hydroxybutyrate, glycollate, maleate, tartrate, methanesulfonate, propanesulfonate, naphthalene-1-sulfonate, naphthalene-2-sulfonate, mandelate and the like salts.

The pharmaceutically acceptable salts of compounds of Formula I can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of Formula I exist, for example the chiral carbon atom which is attached to the imidazole, $R_4$, and $R_5$. This invention is not limited to any particular stereoisomer but includes all possible individual isomers and mixtures thereof.

The synthesis and use of 1,3 imidazoles as angiotensin II antagonists is described in U.S. Pat. No. 5,073,566. U.S. Pat. No. 5,073,566 is herein incorporated by reference.

The tetrazolyl moieties of $R_1$ in Formula I (It is preferred that $R_1$ be protected as a nitrile during the coupling reactions) can be prepared by treating the cyano intermediates with an alkali metal azide such as sodium azide, ammonium chloride or triethylamine hydrochloride, and (optionally) lithium chloride in a nonreactive high boiling solvent such as N,N-dimethylformamide (DMF), preferably at a temperature from about 60°14 125° C. Preferably, tri-(n-butyl)tin azide or tetramethylguanadinium azide, neat or in a solvent such as tetrahydrofuran, dimethoxyethane, diethoxyethane, or the like, may be used in place of the alkali metal azide, ammonium chloride, lithium chloride, and DMF.

The carboxylic acids of Formula I can be prepared by the hydrolysis of the cyano intermediate ($R_1$ is protected as nitrile a during the coupling reactions). The hydrolysis involves the heating of the cyano derivative in an aqueous alcohol in the presence of a base such as sodium or potassium hydroxide. The salts of the carboxylic acid and the tetrazole final product are made by reacting the free acid or tetrazole with the appropriate base by standard procedures.

The compounds of Formula I which contain a sulfonamide in the $R_1$ moiety can be prepared by converting the carboxylic acid of $R_1$ to an acid chloride and then reacting the acid chloride with an alkyl sulfonamide by conventional techniques.

The compounds of Formula I which contain an alkoxy moiety ($R_2$ is an alkoxy) may be readily converted to hydroxy compounds of Formula I. For example, the alkoxy may be cleaved with boron tribromide to form the hydroxy moiety.

The desired products from the disclosed reactions can be isolated by conventional means, and preferably by chromatography. Column chromatography is a preferred method. High pressure column chromatography over silica gel and high pressure reverse phase chromatography offer the most efficient way of purifying the final products. Alternatively, crystallization of the acid, tetrazole, or salts may be employed to purify the desired final product.

One process for preparing the compounds of Formula I involves the alkylation of an imidazole with an alkylating reagent III as summarized in Scheme 1.

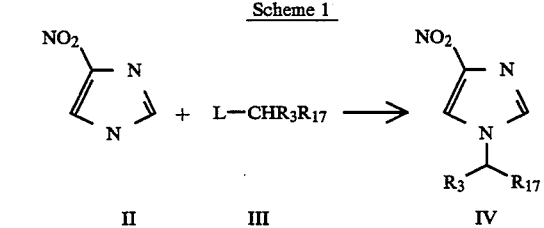

$R_3$ is the same as previously defined. $R_{17}$ is a protected carboxy, such as an ester; or when $R_4$ is (a), $R_{17}$ is a protected imidazolyl. See Greene, T. W., *Protective Groups in Organic Synthesis*, John Wiley & Sons, New York, 1981. To prepare the amides of Formula I, $R_{17}$ is a protected carboxy.

L is a good leaving group such as chloro, bromo, iodo, mesyl, tosyl, and the like. L may also be a hydroxy or a precursor which may be readily converted to a good leaving group by techniques known in the art.

This reaction usually involves approximately equimolar amounts of the two reagents, although other ratios, especially those wherein the alkylating reagent is in excess, are operative. The reaction is best carried out in a polar aprotic solvent wherein the compound is an alkali metal salt or other such alkylation conditions as are appreciated in the art. When the leaving group is bromo or chloro, a catalytic amount of iodide salt, such as potassium iodide may be added to speed the reaction. Preferred reaction conditions include the following: lithium bromide and dimethylformamide, potassium fluoride on alumina in THF, sodium bicarbonate in dimethylformamide, sodium hydride in dimethylformamide, potassium carbonate, potassium iodide, and either methylethyl ketone or acetone. The temperature of the reaction is preferably from about ambient temperature to about the reflux temperature of the reaction mixture. When elevated temperatures are employed, the reaction is generally complete in 1-4 hours.

When preparing the amides of Formula I, the protected carboxy, $R_{17}$, is readily converted to the carboxylic acid and then to the acid halide by techniques known in the art. See Greene, T. W., *Protective Groups in Organic Synthesis*, p. 152. Conversion of the acid to the corresponding acid chloride, for example, can be accomplished upon treatment with a reagent such as thionyl chloride or oxalyl chloride optionally in the presence of an aprotic nonreactive solvent. Preferred combinations include thionyl chloride treatment followed by reaction of the amine in potassium carbonate in tetrahydrofuran, or reaction of oxalyl chloride with the carboxylic acid.

The acid halide of Compound IV may then be reacted with the desired amine to form the amides ($R_4$ is an amide) of the present invention. This reaction is summarized in Scheme 2.

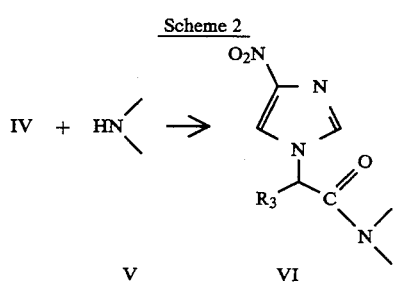

$R_3$ is the same as previously defined. When the amine (Compound V) contains a carbonyl group, it is preferred that carbonyl is protected during the reaction.

The amine employed in this scheme is dependent upon the desired amide of Formula I. For example, to produce a substituted proline derivative, the acid chloride of compound IV may be reacted with a substituted proline methyl ester (V). Likewise, to produce trifluoropropyl amide, the acid halide is reacted with trifluoropropylamine.

The coupling reaction between the acid halide of Compound IV and the amine may be accomplished by any of several known methods. The preferred method in this scheme is to react the acid halide, preferably the acid chloride, with the amine directly in THF or methylene chloride in the presence of triethylamine.

The resulting amide may be converted to the compounds of Formula I by techniques known in the art. See Duncia et al. *J. Org. Chem.* 56:2395–2400 (1991).

Alternatively, Compound III may be converted to the acid chloride and reacted according to Schemes 2 to form the amide. This intermediate may then be alkylated according the conditions described in Scheme 1 to form the nitro imidazole.

The compounds of this invention that contain a carboxamide-type linkage can be prepared according to Scheme 3.

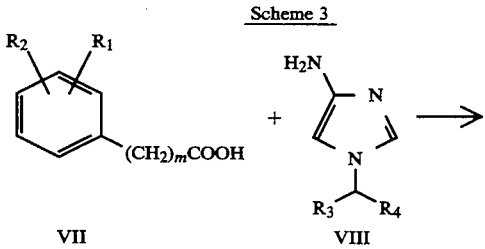

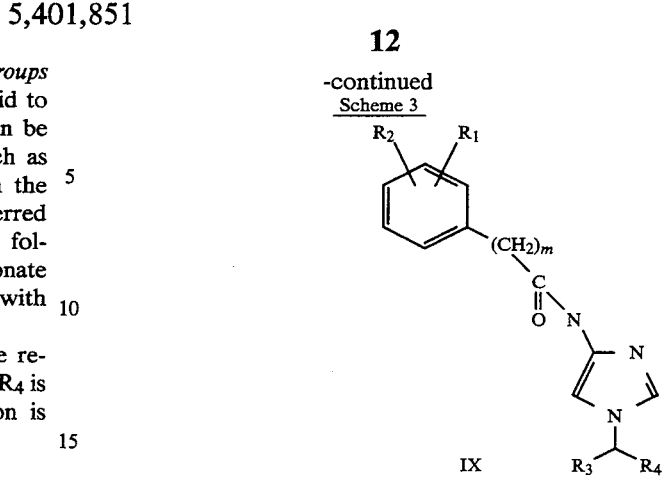

where $R_1$, $R_2$, $R_3$, $R_4$, and m are the same as previously defined.

The transformation as depicted in Scheme 3 above can be accomplished by any of several known methods of coupling carboxylic acids to amines. For example, carboxylic acid VII or XI can be transformed into a corresponding acid halide, particularly an acid chloride, and then reacted with the appropriate amine to provide amides IX or XII as previously discussed.

Alternatively, other amide condensing reagents may also be employed, such as 1,1'-carbonyldiimidazole or 1,3-dicyclohexylcarbodiimide. These reagents are usually employed in a nonreactive high boiling solvent such as dimethylformamide and optionally in the presence of reagents such as diisopropylethylamine, hydroxybenzotriazole, and the like in order to facilitate reaction.

If $R_4$ contains a carboxy moiety, the reaction is best carried out when the carboxy group is protected as an ester. When the coupling is complete the ester may be readily converted into the acid by methods known in the art. For example, the ester moiety may be hydrolyzed with an aqueous base such as 2N NaOH in methanol. The pH lowered to 3.0 with 5N HCL. The acid product may then be extracted by conventional means.

Ketone-containing compounds of Formula I can be prepared by reacting either an anhydride (Compound XIII) or the acid chloride of compound VII with Compound XIV to provide the corresponding ketones XV and XVI, respectively as described in Scheme 4.

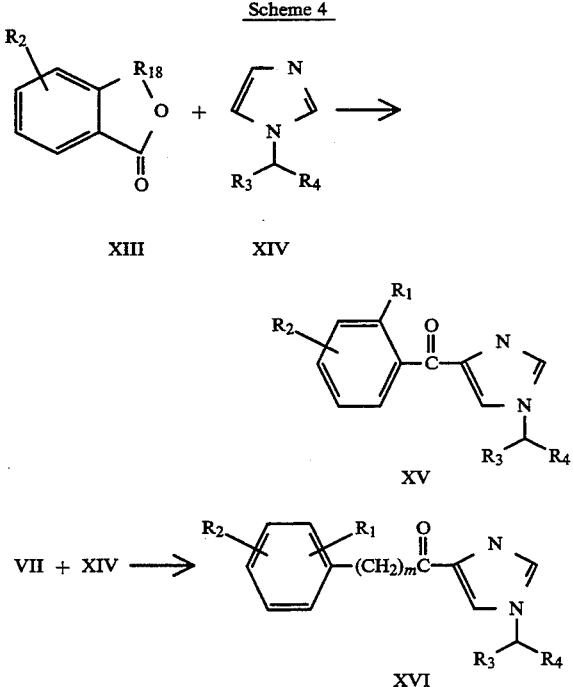

In Scheme 4 above, $R_2$, $R_3$, $R_4$ and m, are the same as previously defined. $R_{18}$ is $SO_2$ or CO. $R_1$ is $SO_3H$ or $CO_2H$.

The reactions portrayed in Scheme 4 are generally known as Friedel-Crafts reactions. The reactions involves reacting approximately equimolar amounts of the acid chloride of compound VII or the anhydride (XIII) with reagent XIV in the presence of a Lewis acid, such as aluminum chloride, in a nonreactive polar solvent such as dimethylformamide or methylene chloride.

In a manner analogous to Scheme 4 above, the ketone containing compounds of Formula I (X is —CO(CH$_2$-)$_m$—) may be prepared by converting a carboxylimidazole to an acid chloride and reacting the acid chloride with a substituted aromatic.

The preferred amide containing compounds of Formula I can be prepared according to the following Scheme 5:

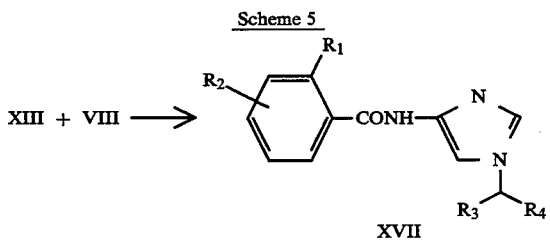

In Scheme 5, the amine is then reacted with the appropriate anhydride (XIII) by mixing the two reagents in one or more nonreactive solvents, such as dimethylformamide. This reaction gives products similar to those found in Scheme 3 above which are, in part, the preferred compounds of Formula I. Alternatively, the anhydride (XIII) can be reacted with one equivalent of an alcohol to provide a monoacid monoester (Compound VII) which may be reacted in accordance with Scheme 3.

The compounds of this invention which contain an amine linkage (X is —NH—) can be prepared by techniques known in the art. For example the Ullman reaction may be employed by reacting with a compound of the formula

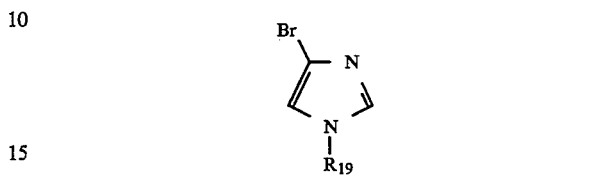

wherein $R_{19}$ is a imidazole protecting group such as a benzyl functionality. The reaction is carried out in the presence of copper bronze or copper chloride in pyridine or dimethylformamide. The resulting product can be deprotected and alkylated in a manner analogous to Scheme 1.

The compounds of this invention that contain a ether linkage (X is —O—) may also be prepared by an Ullman reaction. This reaction is analogous to the preparation of the amine linkage except for beginning with the hydroxy analog of compound X.

The substituted phenoxy proline derivatives may be readily prepared in accordance with Scheme 6.

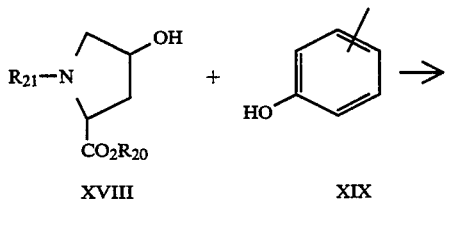

In Scheme 6 above $R_{21}$ is a amino protecting group, preferably carbobenzyloxy; $R_{20}$ is a carboxy protecting group, preferably a $C_1$-$C_4$ alkyl to form an ester. The phenol Compound XIX, is reacted in accordance with this Scheme to prepare the compounds of Formula I wherein $R_{10}$ is a substituted pheny as previously defined.

The reaction protrayed is a known in the art as a Mitsunobu reaction. See Mitsunobu, O., *Synthesis* 1 (1981). Preferably, the reaction is carried out in the presence of triphenylphosphine and diethylazodicarboxylate in an aprotic solvent such as THF. At the completion of this scheme compound XX may be deprotected to form the amine and further reacted in accordance with Scheme 2.

As noted above, the compounds of this invention contain at least one chiral center, that being the carbon atom attached to the imidazole, $R_3$ and $R_4$ substituents. While all of the above schemes address reactions involving racemic reagents and products, each of the reactions can be performed using a chiral starting material to provide a particular enantiomer of interest. Alternatively, particular isomers can be isolated from the racemate by standard methods such as fractional crystallization, high pressure liquid chromatography, reverse phase chromatography and the like. These resolutions can be accomplished either on the final product Formula I, an intermediate, at any stage along the synthetic pathway, or on derivatives of the final product and intermediate. Preferably, Compound IV is separated into its enantiomers before the coupling of Scheme 2. Compound IV is separated by optical resolution employing (−)-cinchonidine as the resolving agent.

Clearly the coupling of the substituted benzoic acid or the substituted anhydride to the imidazolyl, Schemes 3 or 4, may occur at any time in the synthesis. Preferably, the coupling of Scheme 2 occurs prior to Scheme 3 or 4. However, one skilled in the art would appreciate that the order of the reactions is not critical as long as appropriate amino and carboxy protecting groups are employed.

In all of the above schemes, it is preferred that the reactions be carried out wherein all of the $R_1$ groups are protected during the coupling reaction and subsequently deprotected. For example, if $R_1$ is to be a tetrazole, the reaction are best carried out with the cyano intermediate. However, one skilled in the art recognizes that many of these reactions can be performed on the free acid or tetrazole if the appropriate reaction conditions, blocking reagents, or the like are used. Since the $R_1$ moieties are considerably different in their sensitivity to hydrolysis, the sequence for transforming intermediates of the Formula II to final products having both an acid and tetrazole group is not critical.

Compounds II, III, V, VII, VIII, X, XI, XIII, XIV, XVIII, XVIV, and any other reagents required for their transformation, are either commercially available, known in the art, or can be prepared by methods known in the art.

The following examples and preparations are provided merely to further illustrate the invention. The scope of the invention is not construed as merely consisting of the following examples.

In the following examples and preparations, melting point, nuclear magnetic resonance spectra, mass spectra, high pressure liquid chromatography over silica gel, N,N-dimethylformamide, palladium on charcoal, diisobutylaluminum hydride, and tetrahydrofuran are abbreviated M.Pt., NMR, MS, HPLC, DMF, Pd/C, DIBAL and THF, respectively. The terms "NMR" and "MS" indicate that the spectrum was consistent with the desired structure.

Preparation 1

2-Carboxy-6-hydroxybenzenesulfonic acid

Methyl 2-hydroxy-3-methoxybenzoate (0.027 moles, 5.0 g) was added to a suspension of sodium hydride (0.03 moles, 1.45 g of 50% in mineral oil) in 50 ml DMF and stirred at room temperature for 1 hour. Dimethythiocarbamoyl chloride (0.03 moles, 3.73 g) in 40 ml DMF was added dropwise over 1 hour. The reaction was stirred for 18 hours. Ethyl acetate was added. The solution was thoroughly washed with brine, dried and condensed. The residue was purified by HPLC over silica gel eluted with 50% ethyl acetate in hexane to yield 0.9 g of O-(2-carbomethoxy-6-methoxyphenyl)-N,N-dimethylthiocarbamate. (MS).

Calculated for $C_{12}H_{15}NO_4S$: C, 53.52; H, 5.61; N, 5.20. Found: C, 53.35; H, 5.54; N, 5.07.

O-(2-Carbomethoxy-6-methoxyphenyl)-N,N-dimethylthiocarbamate (720 mg) was heated at 220° C. for 100 minutes, and cooled to yield 700 mg of S-(2-carbomethoxy-6-methoxyphenyl)-N,N-dimethylthiocarbamate. (MS)

Calculated for $C_{12}H_{15}NO_4S$: C, 53.52; H, 5.61; N, 5.20. Found: C, 53.74; H, 5.60; N, 4.92.

S-(2-carbomethoxy-6-methoxyphenyl)-N,N-dimethylthiocarbamate (14.4 mmoles, 3.9 g) was dissolved in 66 ml formic acid. Hydrogen peroxide (24 ml of 30%) was added dropwise with cooling when required. The reaction was stirred at room temperature for 16 hours and condensed. Toluene (100 ml) was added to the residue. The toluene solution was concentrated. The solid was slurried in ether and filtered to yield 3.0 g of 2-Carbomethoxy-6-methoxybenzenesulfonic acid dimethylamine salt.

2-Carbomethoxy-6-methoxybenzenesulfonic acid dimethylamine salt (9.0 mmoles, 2.6 g) was added dropwise at −20° C. to a solution of boron tribromide (27 mmoles, 3.8 ml) in 50 ml methylene chloride and stirred at −20° C. for 10 minutes and at room temperature overnight. The reaction was quenched with water. The pH was adjusted to 8.0 using 2N NaOH. The aqueous solution was washed with methylene chloride. The pH of the water layer was adjusted to 1.0 with 2N HCL. The intermediate was extracted with ethyl acetate and condensed. The solid triturated with ethyl acetate and filtered to yield 1.6 g of 2-carboxy-6-hydroxybenzenesulfonic acid.

Preparation 2

N-Carbobenzyloxy-4-trans-hydroxy-L-proline methyl ester.

A solution of silver oxide (I) (1.08 moles, 250 g) in 1500 ml acetone was cooled to −5°–0° C. N-carbobenzyloxy-4-trans-hydroxy-L-proline (0.5 moles, 132.6 g) was added. The solution was stirred for 25 minutes. Methyl iodide (1.2 moles, 170.4 g) was added at −6° C. over 25 minutes. The reaction was stirred at room temperature for 5 hours, filtered, and concentrated. The intermediate was dissolved in ethyl acetate, filtered through silica gel and concentrated. (MS)

Calculated for $C_{14}H_{17}NO_5$: C, 60.21; H, 6.13; N, 5.01. Found: C, 60.40; H, 6.26; N, 5.06.

Preparation 3

N-Carbobenzyloxy-4-cis-phenoxy-L-proline methyl ester.

N-Carbobenzyloxy-4-trans-hydroxy-L-proline methyl ester (0.267 moles, 74.5 g), phenol (0.282 moles, 26.5 g), and triphenylphosphine (0.279 moles, 73.3 g) were dissolved in 750 ml of THF, and cooled to −3° C. Diethyl azidodicarboxylate (0.284 moles, 45 ml) was added dropwise over 2 hours. The reaction was stirred at room temperature overnight and then concentrated. The residue was dissolved in ether, filtered and concentrated. The intermediate was chromatographed over silica gel eluted with a gradient of 0–40% ethyl acetate in hexane to yield 41.0 g. (NMR)

Preparation 4

4-Bromo-t-butoxybenzene.

4-Bromophenol(57.8 moles, 10.0 g) was added to a −30° C. solution of isobutylene (40 ml) and methylene chloride (50 ml) and then cooled to −78° C. Trifluoromethanesulfonic acid (4 mmoles, 0.35 ml) was added. The mixture was held at −78° C. for 4 hours and then allowed to warm to room temperature. Triethylamine (0.5 ml) was added; the solvent was removed. The residue was chromatographed over silica gel eluted with 1% ethyl acetate in hexane to yield 12.4 g. (MS)

Calculated for $C_{10}H_{13}BrO$: C, 52.42; H, 5.72. Found: C, 52.69; H, 5.67.

Preparation 5

4-t-Butoxyphenol.

Sec-butyllithium (53.2 mmoles, 41 ml of 1.3M in hexane) was added dropwise at −78° C. to 4-bromo-t-butoxybenzene (53.2 mmoles, 12.2 g) in 200 ml THF, stirred at −78° C. for 1 hour, and added slowly to a solution of triisopropylborate (58.5 mmoles, 11.0 g) in 50 ml THF while maintaining the temperature below −60° C. The mixture was allowed to warm gradually to −20° C. Chilled acetic acid (80 mmoles,9.6 ml) was added. Hydrogen peroxide (58.5 mmoles, 5.9 ml of 30% diluted with 5 ml water) was added dropwise over 15 minutes while maintaining the temperature below 0° C. After stirring 10 minutes, the solution was washed with ammonium sulfate solution, dried, and concentrated. The residue was triturated with hexane and filtered to yield 4.2 g of 4-t-butoxyphenol. (MS).

Calculated for $C_{10}H_{14}O_2$: C, 72.26; H, 8.49. Found: C, 72.54; H, 8.27.

Preparation 6

Diethyl-(4-hydroxy)-phenethylphosphonate.

A solution of tetraethylmethylenediphosphonate (6.22 g, 21.6 mmol) in 30 mL of anhydrous THF at −30° C. under $N_2$ was treated with nBuLi (15.0 mL, 1.6M solution in hexanes) dropwise via syringe. The resulting solution was warmed to 0° C. for 30 min., and then cooled back to −30° C. 4-Benzyloxybenzaldehyde was then introduced via canula as a solution in 15 mL of anhydrous THF. After warming to room temperature and stirring for 2 hours, the reaction was quenched by pouring into $H_2O$ (200 mL). The aqueous was extracted with ethyl acetate (3×100 mL). The organic was dried ($Na_2SO_4$) and concentrated in vacuo to give an oil. The crude product was chromatographed ($SiO_2$, 25% hexane/ethyl acetate) to give 6.1 g (82%) of the unsaturated phosphonate as a light yellow oil that solidified on standing.

Calculated for $C_{19}H_{23}O_4P$: C, 65.89; H, 6.69. Found: C, 66.15; H, 6.59.

The phosphonate from the previous reaction (6.1 g, 17.5 mmol) was dissolved in 100 mL of absolute ethanol, and treated with 1.15 g of 5% Pd/C. The mixture was hydrogenated at 40 psi for 1 hour, and then passed through a pad of celite. The filtrate was concentrated in vacuo to yield 4.5 g (100%) of diethyl-(4-hydroxy)-phenethylphosphonate as a light yellow oil.

Preparation 7

Diethyl-(4-hydroxy)-phenylphosphate.

4-Benzyloxyphenol (15.0 g, 75 mmol) was dissolved in 100 mL of anhydrous THF and cooled to 0° C. NaH (3.0 g, 75 mmol, 60% dispersion in mineral oil) was then introduced in small portions. When gas evolution ceased, diethylchlorophosphate was introduced dropwise via syringe. After stirring the reaction for 1 hour, the mixture was poured into $H_2O$/ethyl acetate (150 mL ea.). The layers were separated, and the organic washed with 0.1N NaOH (2×100 mL). The organic was dried ($Na_2SO_4$) and concentrated in vacuo to a light yellow liquid. Chromatography ($SiO_2$, first 20% ethyl acetate/hexanes followed by 40% hexanes/ethyl acetate) provided 23.4 g (93%) of diethyl-(4-benzyloxy)-phenyl phosphate as a colorless liquid.

Diethyl-(4-benzyloxy)-phenyl phosphate (15.0 g, 44.7 mmol) was dissolved in 150 mL of 30% ethyl acetate in ethanol, along with 0.5 mL of concentrated HCl. To this solution was added 3.0 g of 10% Pd/C. The mixture was hydrogenated at 1 atm for 18 hours and then passed through a pad of celite to remove the catalyst. The filtrate was concentrated in vacuo, and the residue chromatographed ($SiO_2$, ethyl acetate) to provide 10.4 g (94%) of diethyl-4-hydroxy-phenyl phosphate as an amber liquid.

Preparation 8

Diethyl-(4-hydroxy)-benzenephosphonate

To a solution of 4-benzyloxybromobenzene (10.0 g, 38 mmol) in 150 mL of anhydrous THF at −78° C. under $N_2$ was added nBuLi (26.1 mL, 41.8 mmol, 1.6M in hexanes) dropwise over 30 minutes. After stirring for 15 minutes, diethylchlorophosphate (6.0 mL, 41.8 mmol) was added dropwise via syringe. The resulting mixture was allowed to gradually warm to room temperature whereupon the reaction was quenched by pouring into $H_2O$/ethyl acetate (200 mL ea.). The layers were separated, and the aqueous was extracted with ethyl acetate (2×100 mL). The organic was dried ($Na_2SO_4$), and concentrated in vacuo to a yellow liquid. Chromatography ($SiO_2$, 50–100% ethyl acetate/hexanes) provided 11.1 g (91%) of diethyl-(4-benzyloxy)-benzenephosphonate as a colorless liquid. MS.

Diethyl-(4-benzyloxy)-benzenephosphonate (11.0 g, 34 mmol) was hydrogenated as described in the previous example. Chromatography of the crude reduction product provided 4.3 g (52%) of diethyl-(4-hydroxy)-benzenephosphonate as a light yellow liquid. MS.

Preparation 9

4-(pyrrolidinosulfonyl)-phenol

To a solution of pyrolidine (17 mL, 237 mmol) in 20 mL of $H_2O$ at room temperature was added p-flourobenzenesulfonyl chloride (15 g, 79 mmol) in portions over a 5 minute period. After 1 hour, the solution was diluted with 100 mL of $H_2O$ and extracted with ethyl acetate (3×50 mL). The organic was dried ($Na_2SO_4$) and concentrated in vacuo to give 12.3 g (72%) of 4-(pyrrolidinosulfonyl)flourobenzene as a colorless oil that solidified on standing. This material was used in the following reaction without further purification. MS.

To a solution of benzyl alcohol (6.63 mL, 62.0 mmol) in 200 mL of anhydrous DMF at room temperature was added NaH (2.40 g, 60.0 mmol, 60% dispersion in mineral oil) in small portions. After stirring for 30 minutes, 4-(pyrrolidinosulfonyl)-flourobenzene (11.0 g, 51.2 mmol) was added over a 10 minute period. After 30 minutes, a white precipitate formed. The reaction was then diluted with 100 mL of $H_2$, and the product isolated by vacuum filtration. The solid was dried in vacuo to give 14.85 g (95%) of the 4-(pyrrolidinosulfonyl)-phenylbenzylether as a white solid. MS.

A solution of 4-(pyrrolidinosulfonyl)phenylbenzylether (10.0 g, 33.1 mmol) was dissolved in 100 mL of absolute ethanol. This solution was treated with 2.5 g of 10% Pd/C. The mixture was hydrogenated at 40 psi for 2 hours. The catalyst was then removed by passing the reaction mixture through a pad of celite. The filtrate was concentrated in vacuo to provide 6.8 g (90%) of 4-(pyrrolidinosulfonyl)-phenol as a white solid. MS.

4-(methylaminosulfonyl)-phenol was prepared in a similar manner.

Preparation 10

N-(4-hydroxybenzamido)-L-proline methyl ester.

L-Proline methyl ester hydrochloride (7.2 g, 43.8 mmol) was dissolved in 100 mL of anhydrous DMF at 0° C. To this solution was added triethylamine (4.2 g, 43.8 mmol). After vigorous stirring for 1 hour, the solid triethylamine hydrochloride was removed by filtration. To the filtrate was added 4-benzyloxybenzoic acid (10.0 g, 43.8 mmol) followed by DCC (9.9 g, 48.2 mmol). The reaction mixture was allowed to stir overnight at room temperature. The solid DCU was then removed by filtration, and the filtrated distributed between $H_2O$-/ethyl acetate (300 mL ea.). The organic was washed several times with 200 mL portions of $H_2O$ to remove DMF. The organic was dried ($Na_2SO_4$), and concentrated in vacuo to a solid residue that was chromatographed ($SiO_2$, 15-100% ethyl acetate/hexanes). Isolation provided 5.3 g (35%) of N-(4-benzyloxybenzamido)-L-proline methyl ester as a white solid. MS.

The above amide (10.0 g, 29.4 mmol) dissolved in 75 mL of absolute ethanol. To this solution was added 3 g of 10% Pd/C. The mixture was hydrogenated at 1 atm for 5 hours The catalyst was then removed by passing the reaction through a pad of celite. Concentration of the filtrate provided crude N-(4-hydroxybenzamido)-L-proline methyl ester that was purified by chromatography ($SiO_2$, 30% ethyl acetate/hexanes) to provide 6.3 g (86%) as a white solid. MS.

Preparation 11

(R)-α-hexyl-4-nitro-1H-imidazole-1-acetic acid (−)-cinchonidine salt

To a suspension of 5.89 g (0.02 mol) of (−)-cinchonidine in 80 mL water was added 2.78 mL (2.02 g, 0.02 mol) triethylamine. The mixture was warmed to about 40°-45° C. A solution of 10.21 g (0.04 mol) of a racemic mixture of α-hexyl-4-nitro-1H-imidazole-1-acetic acid in 40 mL technical grade ethanol was added to the warm suspension with stirring. (The pH of the mixture was adjusted to 6.9-7.4 by addition of triethylamine or aqueous hydrochloric acid as required.) The resulting suspension was then heated to about 85° C. The resulting solution was allowed to cool gradually to ambient temperature with slow stirring. The precipitated salt was filtered, washed with about 30 mL of ethanol $-H_2O$ (1:2), and dried at 50° C. in vacuo to constant weight. The reaction produced 9 g of (R)-α-hexyl-4-nitro-1H-imidazole-1-acetic acid (−)-cinchonidine salt. A portion of the product was converted to the free acid and then derivatized as the methyl ester (diazomethane) and analyzed by HPLC on a chiral column. The analysis indicated that the acid derived from the product had an ee of 94%. Recrystallization of the product salt from ethanol-water 1:1 (1:1 volumes) provided 7.4 g of the pure salt, ee>99% (HPLC), M.Pt. 205° C. (dec). (NMR).

Calculated for $C_{30}H_{39}N_5O_5$: C: 65.55; H, 7.15; N, 12.74. Found: C: 65.32; H, 7.25; N, 12.74.

Preparation 12

(R)-α-hexyl-4-nitro-1H-imidazole-1-acetic acid

A 2.80 g portion of the pure cinchonidine salt obtained as described in Example 1 was mixed with 20 mL of 1M HCL. The resulting suspension was extracted with 30 mL of ethyl acetate. The ethyl acetate phase was dried ($MgSO_4$) and concentrated to dryness, providing 0.82 g (63%) of (R)-α-hexyl-4-nitro-1H-imidazole-1-acetic acid. M.Pt. 112°-114° C.

Example 1

N-Ethyl-2-[4-(2-sulfobenzoyl)amino-1H-imidazol-1-yl]octanoamide.

4-Nitroimidazole (0.29 moles, 32.9 g in 30 ml DMF was treated portionwise with sodium hydride (0.29 moles, 11.6 g. 60% in mineral oil) and stirred for 45 minutes. Ethyl 2-bromooctanoate (0.29 moles, 73.1 g) was added dropwise over 1 hour. The reaction was stirred overnight at room temperature, poured onto ice water, and extracted with ethyl acetate. The organic phase was washed with brine, dried and concentrated to yield 91 g of ethyl 2-(4-nitro-1H-imidazol-1-yl)octanoate. (MS)

Ethyl 2-(4-nitro-1H-imidazol-1-yl)octanoate (17 moles, 5.0 g) and ethylamine (20 ml) were stirred in 150 ml ethanol at room temperature for 16 hours. The reaction was added to ice water, extracted with ethyl acetate, washed with water, dried over sodium sulfate and concentrated. The oil crystallized upon standing to yield 3.9 g of N-Ethyl-2-(4-nitro-1H-imidazol-1-yl)octanoamide. (MS).

Calculated. for $C_{13}H_{22}N_4O_3$. ¼ $H_2O$: C, 54.40; H, 7.83; N, 19.52. Found: C, 54.45; H, 7.73; N, 19.12.

N-Ethyl-2-(4-nitro-1H-imidazol-1-yl)octanoamide (5.3 moles, 1.5 g) was reduced by hydrogenation at 40 psi over Pd/C. The reaction was filtered and concentrated. The residue was dissolved in 10 ml THF and added to a solution of 2-sulfobenzoic acid cyclic anhydride (5.3 moles, 0.98 g) in 10 ml THF. After stirring for 10 minutes at room temperature; the product precipitated and was collected by filtration, washed with ether and dried to yield 1.1 g of product. (MS)

M. Pt.: Dec. 235° C. Calculated for $C_{20}H_{28}N_4O_5S$: C, 55.03; H, 6.46; N, 12.83. Found C, 54.75; H, 6.49; N, 13.08.

Example 2

N-Propyl-2-[4-(2-sulfobenzoyl)amino-1H-imidazol-1-yl]octanoamide.

Ethyl 2-(4-nitro-1H-imidazol-1-yl)octanoate (17 moles, 5.0 g) was reacted with propylamine as in Example 1 to yield 2.5 g of N-propyl-2-(4-nitro-1H-imidazol-1-yl)octanoamide. (MS).

N-Propyl-2-(4-nitro-1H-imidazol-1-yl)octanoamide (2.3 mmoles, 0.7 g ) was reduced to the amine and reacted with 2-sulfobenzoic acid cyclic anhydride (2.3 mmoles, 0.423 g) as in Example 1 to yield 0.70 g of product. (MS)

M. Pt.: Dec. 235° C. Calculated for $C_{21}H_{30}N_4O_5S$.1.5 $H_2O$: C, 52.78; H, 6,91; N, 11.71. Found: C, 52.86: H, 6.37; N, 11.16.

Example 3

N-(2,2,2-Trifluoroethyl)-2-[4-(2-sulfobenzoyl)amino-1H- imidazol-1-yl]octanoamide.

2-(4-Nitro-1H-imidazol-1-yl) octanoic acid (7.8 mmoles,2.0 g) was treated with 25 ml oxalyl chloride, concentrated and added to a solution of trifluoroethylamine hydrochloride (7.8 mmoles, 1.06 g) and triethylamine (2 ml) in 50 ml THF. After stirring at room temperature for 16 hours, the mixture was added to ice, extracted with ethyl acetate, dried over sodium sulfate, and concentrated. The intermediate was chromatographed over silica gel to yield 0.6 g of N-(2,2,2-trifluoro)ethyl-2-(4-nitro-1H-imidazol-1-yl)octanoamide. (MS).

Calculated for $C_{11}H_{19}F_3N_4O_3$: C, 46.,43; H, 5.69; N, 16.66. Found: C, 46.56; H, 5.88; N, 16.37.

N-(2,2,2-Trifluoro)ethyl-2-(4-nitro-1H-imidazol-1-yl)octanoamide (1.5 moles, 0.5 g ) was reduce and reacted with 2-sulfobenzoic acid cyclic anhydride (1.4 moles, 0.27 g) as in Example 1 to yield 500 mg of product. (MS)

M. Pt.: Dec. 257°–259° C. Calculated for $C_{20}H_{25}F_3N_4O_5S.H_2O$: C, 47.26; H, 5.35; N, 11.01. Found: H,47.39; H, 5.01; N, 10.82.

Example 4

N-[2-(1-Hydroxy-2-methyl)propyl]-2-[4-(2-sulfobenzoyl)amino-1H-imidazol-1-yl]octanoamide.

2-(4-Nitro-1H-imidazol-1-yl)octanoic acid (3.9 moles, 1.0 g) was converted to the acid chloride and reacted with 2-amino-2-methyl-1-propanol (5.85 mmoles, 0.52 g) as in Example 3 to yield 0.465 g of N-[2-(1-hydroxy-2-methyl)propyl]-2-(4-nitro-1H-imidazol-1-yl)octanoamide.

N-[2-(1-Hydroxy-2-methyl)propyl]-2-(4-nitro-1H-imidazol-1-yl)octanoamide (0.52 moles, 170 mg) was reduced and reacted with 2-sulfobenzoic acid (0.52 moles, 96 mg) as in Example 1 to yield 53 mg of product. (MS)

M. Pt.: 148°–158° C. Calculated for $C_{22}H_{32}N_4O_6S$: C, 54.98; H, 6.71; N, 11.66. Found: C, 51.49; H, 5.53; N, 8.32.

Example 5

2-[[[1-[1-[(2-oxo-1-imidazolidinyl)carbonyl]heptyl]-1H-imidazol-4-yl]amino]carbonyl]benzenesulfonic acid.

Prepared as in Example 3. (MS). Yield of product, 17%.

M. Pt.: 219°–228° C. Calculated for $C_{21}H_{27}N_5O_6S$: C, 52.82; H, 5.70; N, 14.66. Found: C, 51.19; H, 5.54; N, 12.65.

Example 6

2-[[[1-[1-[(2-thioxo-1-imidazolidinyl)carbonyl]-heptyl]-1H-imidazol-4-yl]amino]carbonyl]benzenesulfonic acid.

Prepared as in Example 3. Yield of product, 11%. (MS)

M. Pt.: 203°–211° C. Calculated for $C_{21}H_{27}N_5O_5S$: C, 51.10; H, 5.51; N, 14.19. Found: C, 49.30; H, 5.71; N, 13.69.

Example 7

N-(2-Pyridyl)-2-[4-(2-sulfobenzoyl)amino-1H-imidazol-1-yl]octanoamide.

Prepared as in Example 3. Yield of product, 23%. (MS)

M. Pt.: 165°–173 ° C. Calculated for $C_{23}H_{27}N_5O_5S$ C, 56.89; H, 5.61; N, 14.42. Found: C, 52.50; H, 4.75; N, 9.72.

Example 8

N-(2-Hydroxyphenyl)-2-[4-(2-sulfobenzoyl)amino-1H-imidazol-1-yl]octanoamide.

Prepared as in Example 3. Yield of product, 33%. (MS

M. Pt.: 138°–147° C. Calculated for $C_{24}H_{28}N_4O_6S.1.25$ HCl: C, 52.78; H, 5.40; N, 10.26. Found: C, 52.75; H, 5.23; N, 9.93.

Example 9

N-(2–Carboxyphenyl)-2-[4-(2-sulfobenzoyl)amino-1H-imidazol-1-yl]octanoamide.

N-(2–Carboethoxyphenyl)-2-[4-(2-sulfobenzoyl)amino-1H-imidazol-1-yl]octanoamide. was prepared as in Example 3. The ester (100 mg) was hydrolyzed in 1 ml of 1N NaOH and 0.2 ml methanol for 1 hour at room temperature and acidified with 1N HCl. The solid was filtered and dried for a 88% yield. (MS)

M. Pt.: 163°–168° C. Calculated for $C_{25}H_{28}N_4O_7S.1.25H_2O$: C, 54.49; H, 5.57; N, 10.17. Found: C, 54.58; H, 5.18; N, 9.75.

Example 10

2-[4-(3-Hydroxy-2-sulfobenzoyl)amino-1H-imidazol-1-yl]octanoic acid.

2-Carboxy-6-hydroxybenzenesulfonic acid (1.8 mmole, 400 mg) was dissolved in 15 ml of oxalyl chloride. One drop of DMF was added. The reaction was stirred for 30 minutes at room temperature. The solvent was removed in vacuo, and 20 ml THF added. A solution of ethyl 2-(4-amino-1H-imidazol-1-yl)octanoate (prepared by the reduction of 1.8 mmoles of ethyl 2-(4-nitro-1H-imidazol-1-yl)octanoate in ethanol with 5% Pd/C) in 40 ml THF and 2.0 moles of triethylamine was added dropwise. The reaction was stirred at room temperature for 3 hours; ethyl acetate was added. The solution was washed with water, dried over sodium sulfate and concentrated. The intermediate was slurried in ether, filtered, chromatographed over silica gel eluted with 15% methanol in methylene chloride. The ester was hydrolyzed in 20 ml methanol and 45 ml of 2N NaOH at room temperature for 2 hours. The solvent was removed; water was added. The pH was adjusted to 2.0 using 5N HCL. The product was extracted into ethyl acetate, dried over sodium sulfate and concentrated to yield 2-[4-(3-Hydroxy-2-sulfobenzoyl)amino-1H-imidazol-1-yl]octanoic acid. (MS)

M. Pt.: 238°–240 ° C. Calculated for $C_{18}H_{23}N_3O_7S . \frac{1}{2} H_2O$: C, 49.71; H, 5.50; N, 9.60. Found: C, 49.73; H, 5.38; N, 9.30.

Example 11

1-[1-Oxo-1-[4-(2-sulfobenzoyl)amino-1H-imidazol-1-yl]octyl]-D-proline.

A mixture of stereoisomers was prepared as in Example 21.

Isomer A: Yield 9% (MS) M. Pt.: 145°–150° C. Calculated for $C_{23}H_{30}N_4O_7S$: C, 54.53; H, 5.97; N, 11.06. Found: C, 54.34; H, 6.06; N, 11.03.

Isomer B: Yield 5% (MS) M. Pt.: 148°–155° C. Calculated for $C_{23}H_{30}N_4O_7S$: C, 54.53; H, 5.97; N, 11.06. Found: C, 54.52; H, 6.08; N, 10.93.

Example 12

1-[1-Oxo-2-[4-(2-sulfobenzoyl)amino-1H-imidazol-1-yl]octyl]-4-cis-phenoxy-L-proline.

N-Carbobenzyloxy-4-cis-phenoxy-L-proline methyl ester (0.115 moles, 41 g) was hydrogenated in ethanol over 5% Pd/C and concentrated.

2-Bromooctanoic acid (0.116 moles, 26 g) was added dropwise to a solution of oxalyl bromide (75 g) in 50 ml methylene chloride at ice bath temperature; 1 drop of DMF was added. The solution was stirred at room temperature for 1.5 hours and concentrated. The residue was dissolved in THF and added dropwise at ice bath temperature to a solution of the proline and triethylamine (45 ml) in THF. The reaction was stirred overnight at room temperature, filtered, and concentrated. The oil was dissolved in ethyl acetate, washed with brine, dried over sodium sulfate and concentrated. The product was chromatographed over silica gel eluted with 0–30% ethyl acetate in hexane to yield 26 g 1-(2-bromo-1-oxo)octyl-4-cis-phenoxy-L-proline methyl ester. (NMR)

4-Nitroimidazole (66.3 moles, 7.5 g) was dissolved in 200 ml DMF. Sodium hydride (75 mmoles, 3.0 g of 60% in mineral oil) was added portionwise. The solution was stirred for 1 hour. 1-(2-Bromo-1-oxo)octyl-4-cis-phenoxy-L-proline methyl ester (60 mmoles, 25,6 g) was added. The reaction was stirred at room temperature overnight. The reaction was concentrated; the residue was dissolved in ethyl acetate, washed twice with brine, dried over sodium sulfate and concentrated. The intermediate was chromatographed over silica gel eluted with 25–75% ethyl acetate in hexane.

Isomer A: yield 40% (MS) Calculated for $C_{23}H_{30}N_4O_6$: C, 60.16; H, 6.67; N, 11.95 Found: C, 60.25; H, 6.59; N, 12.21.

Isomer B: yield 16% (MS) Calculated for $C_{23}H_{30}N_4O_6$: C, 60.25; H, 6.59; N, 12.22. Found: C, 60.43; H, 6.63; N, 12.26.

1-[1-oxo-2-(4-nitro-1H-imidazol-1-yl)octyl]-4-cis-phenoxy-L-proline methyl ester, (isomer A, 22.7 moles, 10.4 g) was reduced in ethanol with 5% Pd/C and reacted with 2-sulfobenzoic acid cyclic anhydride (34.2 moles, 6.5 g) as in Example 1 to yield 9.2 g of ester. (MS). The ester was hydrolyzed in 25 ml ethanol and 100 ml 1N sodium hydroxide at room temperature for 1 hour and concentrated. The residue was dissolved in a minimum volume of water. The pH was adjusted to 2.4 using 2N HCL. The precipitate was filtered and dried to yield 6.0 g of product. (MS)

M. Pt.: 180°14 190° C. Calculated for $C_{29}H_{34}N_4O_8S$: C, 58.18; H, 5.72; N, 9.36. Found: C, 58.18; H, 5.78; N, 9.50.

Isomer B was treated in a similar procedure to yield 90% yield of acid.

M. Pt.: >200° C. Calculated for $C_{29}H_{34}N_4O_8S \cdot \frac{1}{2}H_2O \cdot \frac{1}{2}NaCl$: C, 54.69; H, 5.54; N, 8.80. Found: C, 54.21; H, 5.46; N, 8.77.

Example 13

1-[1-Oxo-2-[4-(2-sulfobenzoyl)amino-1H-imidazol-1-yl]heptyl]-4-cis-phenoxy-L-proline 2-(4-nitro-1H-imidazol-1-yl)heptanoic acid (4 mmoles, 0.98 g, prepared as in Example 1) was stirred for 1 hour in 25 ml oxalyl chloride and concentrated. The residue was dissolved in methylene chloride (100 ml) and added dropwise to a solution of 4-cis-phenoxy-L-proline methyl ester (4 mmoles, 0.9 g) and triethylamine (0.56 ml) in 100 ml methylene chloride. The reaction was stirred for 2 hours at room temperature and then added to ice water. The organic layer was washed with water, dried over sodium sulfate, concentrated. The residue was chromatographed over silica gel eluted with a gradient of 50–75% ethyl acetate in hexane.

Isomer A intermediate: yield 41% (MS)
Isomer B intermediate: yield 28%. (MS)
Isomer A intermediate was further reacted as in Example 12 to yield the acid product. (MS).
Calculated for $C_{28}H_{32}N_4O_8S$: C, 57.52; H, 5.52; N, 9.58. Found: C, 56.87; H, 6.13; N, 10.33.

Example 14

1-[1-oxo-2-[4-(2-sulfobenzoyl)amino-1H-imidazol-1yl]-hexyl]-4-cis-phenoxy-L-proline Prepared as in Example 12.

Isomer A: Yield 48%. (MS) M. Pt.: Dec. 215°–220° C. Calculated for $C_{27}H_{30}N_4O_8S \cdot H_2O \cdot NaCl$: C, 50.12; H, 4.98; N, 8.66. Found: C, 49.79; H, 4.81; N, 8.71.

Isomer B: Yield 29%. (MS). M. Pt.: Dec. 210° C. Calculated for $C_{27}H_{30}N_4O_8S \cdot H_2O$: C, 55.09; H, 5.48; N, 9.52. Found: C, 55.39; H, 5.36; N, 9.15.

Example 15

1-[1-oxo-2-[4-(2-sulfobenzoyl)amino-1H-imidazol-1-yl]-8,8,8-trifluorooctyl]-4-cis-phenoxy-L-proline.

6-Bromohexanoic acid (0.51 moles, 100 g) was heated under $SF_4$ at 130° C. for 8 hours. Methylene chloride was added. The solution was filtered and concentrated. The resulting black oil, 6-Bromo-1,1,1-trifluorohexane, was distilled.

B Pt. 158°–164° C./760 mm.

6-Bromo-1,1,1-trifluorohexane (0.228 moles, 50 g) was added to a solution of sodium iodide(51 g) in 250 ml acetone and stirred for 1 hour at room temperature. The solution was filtered and concentrated. The residue was slurried in ether, filtered and concentrated to yield 56 g, 92% of iodide. Ethyl acetoacetate (0.125 moles, 16.45 g) was added slowly to sodium hydride(0.126 moles, 5.06 g of 60% in mineral oil). The iodide (0.115 moles, 30.6 g) was added. The reaction was heated at 50° C. for 16 hours and then poured into ice water. The intermediate was extracted with ethyl acetate, dried over sodium sulfate and concentrated. The residue was chromatographed over silica gel eluted with ethyl acetate in hexane to yield 13.3 g of ethyl 6,6,6-trifluorohexylacetoacetate. (MS).

Ethyl 6,6,6-trifluorohexylacetoacetate was added at −35° C. to a solution of sodium (50 moles, 1.15 g) in 150 ml ethanol and stirred for 15 minutes. N-Bromosuccinimide (50 moles, 8.9 g) was added. The solution was allowed to warm to room temperature and stirred for 2.5 hours. The mixture was poured into water. The intermediate was extracted with hexane. The solvent was removed. The oil was chromatographed over silica gel eluted with hexane to yield 13.6 g of ethyl 2-bromo-8,8,8-trifluorooctanoate. (MS).

4-Nitroimidazole (43 mmoles, 4.86 g) was reacted with sodium hydride(43 moles, 1.72 g) and then ethyl 2-bromo-8,8,8-trifluorooctanoate (43 moles, 13.2 g) as in Example 1. The ester was hydrolyzed in 10 ml methanol and 30 ml 2N NaOH to yield a quantitative yield of 2-(4-nitro-1H-imidazol-1-yl)-8,8,8-trifluorooctanoic acid. (NMR)

The acid was further reacted as in Example 13 to produce the stereoisomers of 1-[1-oxo-2-(4-nitro-1H-imidazol-1-yl)-8,8,8-trifluorooctyl]-4-cis-phenoxy-L-proline methyl ester. (NMR) The isomers were separated as in Example 1; A isomer was further reacted as previously described. The product was chroma to graphed over silica gel eluted with 5% methanol in chloroform to produce 1-[1-oxo-2-[4-(2-sulfobenzoyl)amino-1H-imidazol-1-yl]-8,8,8trifluorooctyl]-4-cis-phenoxy-L-proline.

Isomer A: Yield 13%. (MS) Calculated for $C_{29}H_{30}F_3N_4O_8S$. 0.6HCl: C, 51.64; H, 4.72; N, 8.31. Found: C, 51.58; H, 4.80; N, 8.18.

Example 16

1-[1-Oxo-2-[4-(2-sulfobenzoyl)amino-1H-imidazol-1-yl]-7,7,7-trifluoroheptyl]-4-cis-phenoxy-L-proline.

2-(4-Nitro-1H-imidazol-1-yl)-7,7,7-trifluoroheptanoic acid was prepared as in Example 15. (NMR). The acid was further reacted as in Example 13 to produce 1-[1-Oxo-2-(4-nitro-1H-imidazol-1-yl)-7,7,7-trifluoroheptyl]-4-cis-phenoxy-L-proline methyl ester. (NMR)

The ester was reacted as in Example 15 to produce 1-[1-Oxo-2-[4-(2-sulfobenzoyl)amino-1H-imidazol-1-yl]-7,7,7-trifluoroheptyl]-4-cis-phenoxy-L-proline.

Isomer A: yield 21%, (MS). Calculated for $C_{28}O_{29}F_3N_4O_8S$. 0.9HCl: C, 50.09; H, 4.49; N, 8.44. Found: C, 50.13; H, 4.66; N, 8.44.

Isomer B: yield 26%, (MS). Calculated for $C_{28}O_{29}F_3N_4O_8S$: C, 52.66 H, 4.58; N, 8.77. Found: C, 52.80; H, 4.85; N, 8.63.

Example 17

1-[1-Oxo-2-[4-(2-sulfobenzoyl)amino-1H-imidazol-1-yl]octyl]-4-cis-(3-pyridyloxy)-L-proline.

4-cis-(3-Pyridyloxy)-L-proline methyl ester (5.32 mmoles, 1.18 g (prepared as in Preparation 3 followed by the deprotection of N-carbobenzyloxy-4-cis-(3-pyridyloxy)-L-proline methyl ester in ethanol with 5% Pd/C), 2-(4-nitro-1H-imidazol-1-yl)octanoic acid (5.32 mmoles, 1.36 g), and hydroxybenzotriazole(5.85 mmoles, 0.8 g) were dissolved in 5 ml DMF. After 5 minutes dicyclohexylcarbodiimide (5.85 mmoles, 1.21 g) was added. The reaction was stirred for 60 hours at room temperature. Ethyl acetate (15 ml) was added. The solution was filtered, washed with water, dried over sodium sulfate and concentrated. The residue was chromatographed over silica gel eluted with 1% methanol in chloroform to produce 1-[1-Oxo-2-(4-nitro-1H-imidazol-1-yl)octyl]-4-cis-(3-pyridyloxy)-L-proline methyl ester.

Isomer A: 0.63 g; (MS)
Isomer B, 0.37 g; (MS)

Each isomer was reacted as in Example 1 to yield 1-[1-Oxo-2-[4-(2-sulfobenzoyl)amino-1H-imidazol-1-yl]octyl]-4-cis-(3-pyridyloxy)-L-proline.

Isomer A: Yield 3 %, (MS).
Isomer B: Yield 3 %, (MS).

Example 18

1-[1-oxo-2-[4-(2-sulfobenzoyl)amino-1H-imidazol-1-yl]octyl-4-cis-(4-methoxyphenyloxy)-L-proline N-Carbobenzyloxy-4-cis-(4-methoxyphenoxy)-L-proline methyl ester (prepared as in Preparation 3) was reacted as in Example 12 to produce 1-[1-oxo-2-[4-(2-sulfobenzoyl)amino-1H-imidazol-1-yl]octyl-4-cis-(4-methoxyphenoxy)-L-proline.

Isomer A: yield 42% (MS) Calculated for $C_{30}H_{36}N_4O_9S.0.5 H_2O$: C, 56.50; H, 5.80; N, 8.78. Found: C, 56.36; H, 6.12; N, 8.67.

Example 19

1-[1-Oxo-2-[4-(2-sulfobenzoyl)amine-1H-imidazol-1-yl]octyl]-4-cis-(4-hydroxyphenoxy)-L-proline N-Carbobenzyloxy-4-cis-(4-t-butoxyphenoxy)-L-proline methyl ester (prepared as in Preparation 3) was reacted as in Example 13 to produce 1-[1-oxo-2-(4-nitro-1H-imidazol-1-yl)octyl-4-cis-(4-t-butoxyphenoxy)-L-proline.

Isomer A': Yield, 34%. (MS) Calculated for $C_{27}H_{38}N_4O_7$. 0.8 H$_2$O: C, 59.50; H, 7.32; N, 10.27. Found: C, 59.60; H, 7.04; N, 9.98.

Isomer B': Yield, 33%. (MS). Calculated for $C_{27}H_{38}N_4O_7$: C, 61.12; H, 7.22; N, 10.56. Found: C, 61.37; H, 7.32; N, 10.59.

Isomer A' was further reacted as in Example 12 to produce 1-[1-Oxo-2-[4-(2-sulfobenzoyl)amino-1H-imidazol-1-yl]octyl]-4-cis-(4-t-butoxyphenoxy)-L-proline ethyl ester. The t-butoxyphenoxy proline ethyl ester was stirred in trifluoroacetic acid (TFA, 3 ml) for three hours at room temperature. The excess TFA was removed; and the residue hydrolyzed as in Example 12 to yield the product.

Isomer A: (MS) M. Pt.: 180°–194° C. Calculated for $C_{29}H_{34}N_4O_9S$: C, 56.67; H, 5.58; N, 9.12. Found: C, 56.95; H, 5.69; N, 8.93.

Example 20

1-[1-oxo-2-[4-(2-carboxy-3-hydroxybenzoyl)amino-1H-imidazol-1-yl]octyl]-4-cis-phenoxy-L-proline.

Isomer A of 1-[1-oxo-2-(4-nitro-1H-imidazol-1yl)octyl]-4-cis-phenoxy-L-proline (1.09 mmoles, 0.5 g, prepared as in Example 12) was hydrogenated in ethanol over 5% Pd/C, filtered and concentrated. The residue was dissolved in 25 ml acetonitrile and added to a solution of 3-hydroxyphthalic anhydride in 25 ml acetonitrile. After stirring at room temperature for 2 hours, the solid was collected and dried to yield 21% ester. (MS). The ester (0.24 mmoles, 0.14 g) was warmed for 15 minutes in 5 ml ethanol and 5 ml 1N NaOH, stirred at room temperature for 1 hour, and condensed. Water (20 ml) was added to the residue. The pH was adjusted to 3.0 using 5 N HCL. The precipitate was filtered and dried to yield 86% of 1-[1-oxo-2-[4-(2-carboxy-3-hydroxybenzoyl) amino-1H-imidazol-1-yl]octyl]-4-cis-phenoxy-L-proline. (MS)

M. Pt.: 155°–170° C. Calculated for $C_{30}H_{34}N_4O_8$: C, 62.27; H, 5.92; N, 9.68. Found: C, 62.01; H, 5.66; N, 9.62.

Example 21

1-[1-Oxo-2-[4-(2-sulfobenzoyl)amino-1H-imidazol-1-yl]octyl]-L-proline

Diisopropylethylamine (39.6 mmoles, 5.1 g) was added to a solution of L-proline benzyl ester hydrochloride (39.6 moles, 10.1 g) in 20 ml DMF at 0° and stirred for 1 hour. The solution was added to 2-(4-nitro-1H-imidazol-1-yl)octanoic acid (39.6 mmoles, 10.1 g) and hydroxybenzotriazole (43 mmoles, 5.8 g) in 10 ml DMF, and stirred for 30 minutes. Dicyclohexylcarbodiimide (43 mmoles, 8.97 g) was added portionwise over 2 hours. Ethyl acetate (50 ml) was added. The solution was filtered, dried over sodium sulfate and concentrated. The oil was chromatographed over silica gel eluted with 40% ethyl acetate in hexane to yield 5.32 g of 1-[1-oxo-2- (4-Nitro-1H-imidazol-1-yl)octyl]-L-proline benzyl ester.

1-[1-Oxo-1-(4-nitro-1H-imidazol-1-yl)octyl]-L-proline benzyl ester (2.46 moles, 0.89 g, isomer A) was reduced in ethanol with 0.5 g of 10% Pd/C. The catalyst was filtered; and solution concentrated. The amine was dissolved in 5 ml of THF. Sulfobenzoic anhydride (2.46 moles, 0.46 g) was added and stirred for 30 minutes. The solvent was removed; the residue triturated with ether. The solid was dissolved in 3 ml of 1N NaOH and stirred for 2 hours, acidified to pH 3.5 with 1N HCl. The product was filtered and chromatographed over reverse phase silica gel to yield 96 mg of 1-[1-oxo-2-[4-(2-sulfobenzoyl)amino-1H-imidazol-1-yl]octyl]-L-proline. (MS).

M. Pt.: 190°–195° C. Calculated for $C_{23}H_{30}N_4O_7S$: C, 54.53; H, 5.97; N, 11.06. Found: C, 54.46; H, 6.03; N, 11.08.

Isomer B was treated in a similar manner to yield 115 mg. (MS)

M Pt. 163°–170 ° C. Found: C, 54.37; H, 6.00; N, 11.96.

The following examples were prepared in a similar manner and further illustrate the synthesis of the compounds of the invention defined by the formula:

| Example | R | Yield (%) | M.P. (°C.) | Elemental Analysis |
|---|---|---|---|---|
| 22 | Methyl | 4 | 146–170 | Calcd for $C_{30}H_{36}N_4O_8S \cdot 0.5H_2O$: C, 58.01; H, 5.96; N, 9.02 Found: C, 58.14; H, 6.16; N, 9.32. |
| 23 | Ethyl | 3 | 155–165 | Calcd for $C_{31}H_{38}N_4O_8S \cdot 1.0H_2O$: C, 57.75; H, 6.25; N, 8.68 Found: C, 57.48; H, 6.08; N, 8.80. |
| 24 | iPropyl | 2 | 175–185 (dec) | Calcd for $C_{32}H_{40}N_4O_8S$: C, 59.98; H, 6.29; N, 8.74 Found: C, 59.83; H, 6.46; N, 8.51. |
| 25 | tButyl | 3 | 162–270 | Calcd for $C_{33}H_{42}N_4O_8S$: C, 60.53; H, 6.47; N, 8.56 Found: C, 60.92; H, 6.95; N, 7.73. |
| 26 | cyclopentyl | 2 | 172–180 | Calcd for $C_{34}H_{42}N_4O_8S$: C, 61.24; H, 6.35; N, 8.40 Found: C, 61.50; H, 6.47; N, 8.47. |
| 27 | phenyl | 3 | 154–165 | Calcd for $C_{35}H_{38}N_4O_8S$: C, 62.30; H, 5.68; N, 8.30 Found: C, 62.41; H, 5.83; N, 8.07. |
| 28 | F | 5 | 150–190 | Calcd for $C_{29}H_{33}F_3N_4O_8S \cdot 1.5H_2O$: C, 55.63; H, 5.43; N, 8.90 Found: C, 55.68; H, 5.67; N, 8.42. |
| 29 | $CF_3$ | 4 | 155–162 | Calcd for $C_{30}H_{33}N_4O_8S \cdot 1.5H_2O$: C, 51.94; H, 5.19; N, 8.00 Found: C, 52.33; H, 4.87; N, 7.64. |
| 30 | $SCH_3$ | 2 | 162–168 | Calcd for $C_{30}H_{36}N_4O_8S_2$: C, 55.89; H, 5.63; N, 8.40. Found: C, 55.68; H, 5.56; N, 8.69 |
| 31 | $S(O)CH_3$ | 3 | 160–170 | Calcd for $C_{30}H_{36}N_4O_8S \cdot 1.5H_2O$: C, 51.94; H, 5.19; N, 8.00 Found: C, 52.33; H, 4.87; N, 7.64. |
| 32 | $SO_2CH_3$ | 5 | 170–182 | Calcd for $C_{30}H_{36}N_4O_{10}S_2$: C, 53.24; H, 5,36; N, 8.28 Found: C, 53.30; H, 5.52; N, 8.25. |
| 33 | $CO_2H$ | 4 | 185–195 | Calcd for $C_{30}H_{34}N_4O_{10}S \cdot 3.0H_2O$: C, 51.71; H, 5.78; N, 8.04 Found: C, 51.57; H, 5.47; N, 7.66. |
| 34 | $CONH_2$ | 5 | 141–151 | Calcd for $C_{30}H_{35}N_5O_9S$: C, 56.15; H, 5.50; N, 10.91 Found: C, 54.82; H, 5.87; N, 12.46. |
| 35 | $CH_2OH$ | 1 | 160–172 | Calcd for $C_{30}H_{36}N_4O_9S$: C, 57.31; H, 5.77; N, 8.91 Found: C, 56.85; H, 5.81; N, 9.31 |
| 36 | $CH_2CO_2H$ | 5 | 160–175 | Calcd for $C_{31}H_{36}N_4O_{10}S \cdot 0.5H_2O$: C, 55.88; H, 5.55; N, 8.42 Found: C, 55.46; H, 5.81; N, 8.71 |
| 37 | $(CH_2)_2CO_2H$ | 3 | 140–148 | Calcd for $C_{32}H_{38}N_4O_{10}S$: C, 57.30; H, 5.71; N, 8.35 Found: C, 57.03; H, 5.83; N, 8.29 |
| 38 | 1-imidazole | 2 | 175–180 (dec) | Calcd for $C_{32}H_{36}N_6O_8S$: C, 57.82; H, 5.46; N, 12.64 Found: C, 56.57; H, 5.92; N, 13.53. |

-continued

| Example | R | Yield (%) | M.P. (°C.) | Elemental Analysis |
|---|---|---|---|---|
| 39 | -SO$_2$-N(pyrrolidine) | | 175-181 | Calcd for C$_{33}$H$_{41}$N$_5$O$_{10}$S$_2$:<br>C, 54.16; H, 5.65; N, 9.57.<br>Found: C, 54.24; H, 5.90; N, 9.49 |
| 40 | -SO$_2$-NHCH$_3$ | | 195-200 | Calcd for C$_{30}$H$_{37}$N$_5$O$_{10}$S$_2$:<br>C, 52.09; H, 5.39; N, 10.12.<br>Found: C, 52.26; H, 5.56; N, 9.93. |
| 41 | (methyloxazole-CO$_2$H) | | 165-170 | Calcd for C$_{33}$H$_{35}$N$_5$O$_{11}$S.0.25HCl:<br>C, 55.14; H, 4.94; N,<br>Found: C, 55.30; H, 5.14; N, 9.75 |
| 42 | -CH$_2$CH$_2$CH$_2$-P(O)(OH)$_2$ | | 230-240 (dec) | Calcd for C$_{31}$H$_{39}$N$_4$O$_{11}$PS.1.5HCl:<br>C, 48.90; H, 5.36; N, 7.36<br>found: C, 49.21; H, 5.38; N, 7.15 |
| 43 | -O-P(O)(OH)$_2$ (with ethyl) | | 177 (dec) | ** |
| 44 | -P(O)(OH)$_2$ | | 185 (dec) | ** |
| 45 | -N(triazole) | | 185° C. (dec) | Calcd for C$_{31}$H$_{35}$N$_7$O$_8$S 0.62HCL:<br>C, 54.09; H, 5.22; N,.14.24<br>Found: C, 54.12; H, 5.25; N, 14.09. |
| 46 | -CH$_2$CH$_2$-C(O)-N(CH$_3$)-CH$_2$-CO$_2$H | | 157-162° C. (dec) | Calcd for C$_{34}$H$_{41}$N$_5$O$_{11}$PS:<br>C, 56.11; H, 5.67; N, 9.62<br>Found: C, 56.40; H, 5.65; N, 9.32. |
| 47 | -CH$_2$-C(O)-N(pyrrolidine-CO$_2$H) | | 185-190° C. (dec) | ** |

| | 48 | Ethyl | 3 | 155-165 | Calcd for C$_{31}$H$_{38}$N$_4$O$_9$S.1.0H$_2$O:<br>C, 56.3; H, 6.05; N, 8.47<br>Found: C, 56.6; H, 5.93; N, 8.71 |
|---|---|---|---|---|---|
| | 49 | iPropyl | 4 | 138-145 | Calcd for C$_{32}$H$_{40}$N$_4$O$_9$S:<br>C, 58.52; H, 6.14; N, 8.53<br>Found: C, 58.62; H, 6.23; N, 8.45. |
| | 50 | nButyl | 2 | 134-155 | Calcd for C$_{33}$H$_{42}$N$_4$O$_9$S:<br>C, 59.09; H, 6.31; N, 8.35<br>Found: C, 58.85; H, 6.31; N, 8.30. |
| | 51 | iButyl | 7 | 160-165 (dec) | Calcd for C$_{33}$H$_{42}$N$_4$O$_9$S.0.17HCl:<br>C, 58.44; H, 6.28; N, 8.28.<br>Found: C, 58.48; H, 6.46; N, 8.65 |

-continued

| Example | R | Yield (%) | M.P. (°C.) | Elemental Analysis |
|---|---|---|---|---|
| 52 | tButyl | 3 | 170–175 (dec) | Calcd for $C_{33}H_{42}N_4O_9S$: C, 59.09; H, 6.31; N, 8.35 Found: C, 58.97; H, 6.22; N, 8.25 |
| 53 | $CF_3$ | 5 | 163–165 (dec) | Calcd for $C_{30}H_{33}F_3N_4O_9S$: C, 52.78; H, 4.87; N, 8.21 Found: C, 53.00; H, 5.01; N, 8.10. |
| 54 | cyclopentyl | 7 | 170–175 (dec) | Calcd for $C_{34}H_{42}N_4O_9S \cdot 0.4HCl$: C, 58.56; H, 6.13; N, 8.03. Found: C, 58.61; H, 6.05; N, 8.18. |
| 55 | cyclopropyl-methyl | 5 | 163–170 (dec) | Calcd for $C_{33}H_{40}N_4O_9S$: C, 59.27; H, 6.03; N, 8.38 Found: C, 59.01; H, 5.87; N, 8.55. |
| 56 | cyclohexyl-methyl | 11 | 170–174 (dec) | Calcd for $C_{36}H_{46}N_4O_9S \cdot 9.73HCl$: C, 58.63; H, 6.39; N, 7.60. Found: C, 58.66; H, 6.13; N, 7.57. |
| 57 | $CH_2CO_2H$ | 8 | 161–164 | Calcd for $C_{31}H_{36}N_4O_{11}S$: C, 55.35; H, 5.39; N, 8.33 Found: C, 55.51; H, 5.57; N, 8.12. |
| 58 | $C(CH_3)_2CO_2H$ | 1 | 167–175 (dec) | Calcd for $C_{33}H_{40}N_4O_{11}S \cdot 0.72HCl$: C, 54.55; H, 5.65; N, 7.71 Found: C, 54.43; H, 5.59; N, 8.11. |

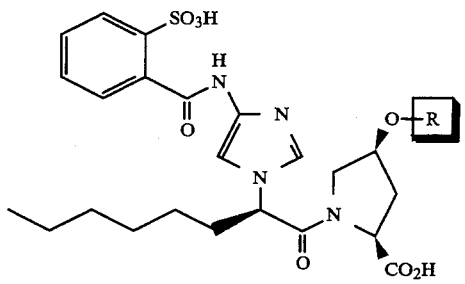

| 59 | ![benzodioxole] | 5 | 169–175 (dec) | Calcd for $C_{30}H_{34}N_4O_{10}S \cdot 0.5HCl$: C, 54.52; H, 5.26; N, 8.48 Found: C, 54.35; H, 5.25; N, 8.25. |
| 60 | ![dimethoxyphenyl] | 2 | 152–162 | Calcd for $C_{31}H_{38}N_4O_{10}S \cdot 0.5HCl$: C, 54.52; H, 5.26; N, 8.48 Found: C, 54.35; H, 5.25; N, 8.25. |
| 61 | ![naphthyl] | 5 | 170–175 | Calcd for $C_{33}H_{36}N_4O_{10}S \cdot 0.5H_2O$: C, 59.37; H, 5.70; N, 8.40 Found: C, 59.06; H, 5.68; N, 8.64. |
| 62 | ![methoxynaphthyl] | 2 | 160–180 | Calcd for $C_{34}H_{38}N_4O_9S \cdot 0.5H_2O$: C, 59.30; H, 5.71; N, 8.14 Found: C, 59.40; H, 5.60; N, 7.89. |
| 63 | ![carboxynaphthyl] | 8 | >200 | Calcd for $C_{34}H_{36}N_4O_{10}S \cdot 0.75NaCl$: C, 55.44; H, 4.92; N, 7.61 Found: C, 55.18; H, 5.05; N, 7.79. |
| 64 | ![naphthyl] | 4 | 170–190 | Calcd for $C_{33}H_{36}N_4O_8S \cdot 1.0H_2O$: C, 59.37; H, 5.70; N, 8.40 Found: C, 59.76; H, 5.70; N, 8.45. |
| 65 | ![benzofuryl] | 1 | 185–190 (dec) | Calcd for $C_{32}H_{35}N_5O_8S \cdot 1.0HCl$: C, 56.01; H, 5.29; N, 10.21 Found: C, 56.38; H, 5.65; N, 10.21. |

-continued

| Example | R | Yield (%) | M.P. (°C.) | Elemental Analysis |
|---|---|---|---|---|
| 66 | 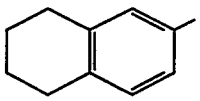 | 9 | 170–175 (dec) | Calcd for $C_{32}H_{38}N_4O_8S \cdot 1.0HCl$: C, 56.92; H, 5.82; N, 8.30 Found: C, 57.33; H, 5.84; N, 8.11. |
| 67 | 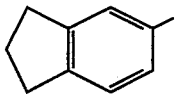 | 7 | 175–182 | Calcd for $C_{33}H_{40}N_4O_8S \cdot 0.6HCl$: C, 58.75, H, 6.07; N, 8.30 Found: C, 58.67; H, 6.00; N, 8.53. |
| 68 | 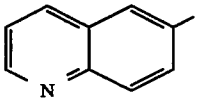 | 7 | 170–180 (dec) | Calcd for $C_{31}H_{34}N_4O_9S \cdot 1.2HCl$: C, 54.56; H, 5.20; N, 8.20 Found: C, 54.44; H, 5.16; N, 8.44. |
| 69 | 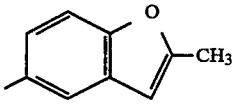 | 6 | 170–178 (dec) | Calcd for $C_{33}H_{30}N_4O_9S \cdot 0.5HCl$: C, 57.28; H, 5.48; N, 8.48 Found: C, 57.27; H, 5.49; N, 8.35. |
| 70 | 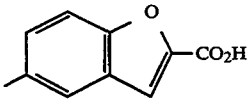 | 3 | 193–200 (dec) | Calcd for $C_{32}H_{34}N_4O_{11}S$: C, 56.30; H, 5.02; N, 8.21 Found: C, 56.19; H, 5.10; N, 8.21. |
| 71 | 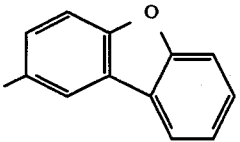 | 14 | 173–180 (dec) | Calcd for $C_{35}H_{36}N_4O_9S \cdot 0.52HCl$: C, 59.45; H, 5.20; N, 7.92 Found: C, 59.36; H, 5.38; N, 8.20. |
| 72 | 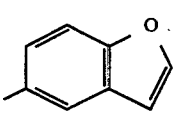 | 3 | 168–172 (dec) | Calcd for $C_{31}H_{35}N_4O_8S_2 \cdot 3.5HCl$: C, 47.59; H, 4.83; N, 7.16 Found: C, 47.52; H, 4.63; N, 7.32. |
| 73 | 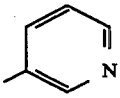 | 3 | 180–183 (dec) | Calcd for $C_{28}H_{33}N_5O_8S_1 \cdot 3.0HCl$: C, 47.43; H, 4.88; N, 9.90 Found: C, 47.01; H, 4.88; N, 10.49. |
| 74 | 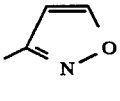 | 6 | 225–230 (dec) | Calcd for $C_{26}H_{31}N_5O_9S_2 \cdot .75HCl$: C, 50.62; H, 5.19; N, 11.35 Found: C, 50.62; H, 5.18; N, 11.19. |

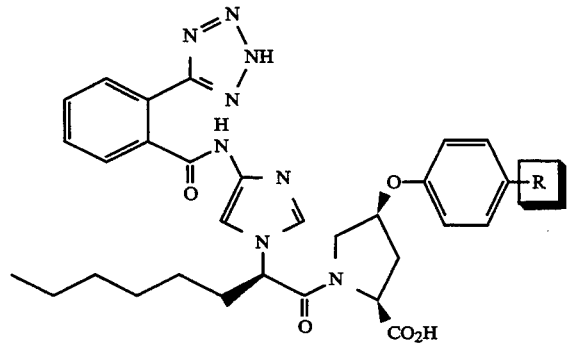

| | | | | |
|---|---|---|---|---|
| 75 | OMethyl | 3 | 160–170 | Calcd for $C_{31}H_{36}N_8O_6 \cdot 1.5H_2O$: C, 57.80; H, 6.10; N, 17.40 Found: C, 57.68; H, 5.75; N, 17.32. |
| 76 | OtButyl | 17 | 149–156 (dec) | Calcd for $C_{34}H_{42}N_8O_6 \cdot 0.5HCl$: C, 60.32; H, 6.33; N, 16.55 Found: C, 60.46; H, 6.22; N, 16.69. |
| 77 | $CH_2CO_2H$ | 5 | 135–146 | Calcd for $C_{32}H_{36}N_8O_7 \cdot 1.0H_2O$: C, 57.90; H, 5.70; N, 16.90 |

-continued

| Example | R | Yield (%) | M.P. (°C.) | Elemental Analysis |
|---|---|---|---|---|
| 78 | CO$_2$H | 5 | 157–178 | Found: C, 57.87; H, 5.81; N, 15.40.<br>Calcd for C$_{31}$H$_{34}$N$_8$O$_7$:<br>C, 59.04; H, 5.43; N, 17.77<br>Found: C, 58.88; H, 5.54; N, 17.54. |
| 79 | OCH$_2$CO$_2$H | 4 | 175–190 | Calcd for C$_{32}$H$_{36}$N$_8$O$_8$.1.5H$_2$O:<br>C, 55.89; H, 5.72; N, 16.29<br>Found: C, 55.64; H, 5.37; N, 16.18. |

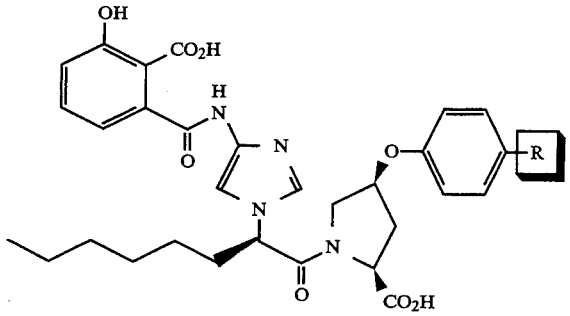

| Example | R | Yield (%) | M.P. (°C.) | Elemental Analysis |
|---|---|---|---|---|
| 80 | Ethyl | 2 | 133–143 | Calcd for C$_{30}$H$_{38}$N$_4$O$_8$.1H2O:<br>C, 61.5; H, 6.45; N, 8.97;<br>Found: C, 61.0; H, 6.29; N, 9.05 |
| 81 | OH | 1 | 135–140 (dec) | Calcd for C$_{30}$H$_{34}$N$_4$O$_9$<br>C, 60.60; H, 5.76; N, 9.42<br>Found: C, 48.81; H, 4.65; N, 7.14. |
| 82 | OMethyl | 4 | 127–135 | Calcd for C$_{31}$H$_{36}$N$_4$O$_9$.1.0H$_2$O:<br>C, 59.41; H, 6.06; N, 8.94<br>Found: C, 59.41; H, 5.96; N, 9.05. |
| 83 | OEthyl | 5 | 133–137 | Calcd for C$_{32}$H$_{38}$N$_4$O$_9$.1.0H$_2$O:<br>C, 59.93; H, 6.24; N, 8.74<br>Found: C, 60.06; H, 6.14; N, 9.15. |
| 84 | OnButyl | 2 | 145–151 | Calcd for C$_{34}$H$_{42}$N$_4$O$_9$.1.5H$_2$O:<br>C, 60.26; H, 6.60; N, 8.26<br>Found: C, 59.97; H, 6.28; N, 7.95. |
| 85 | CO$_2$H | 3 | 155–160 | Calcd for C$_{31}$H$_{34}$N$_4$O$_{10}$2.0H$_2$O:<br>C, 56.52; H, 5.81; N, 8.50<br>Found: C, 56.78; H, 5.49; N, 8.47. |
| 86 | CH$_2$CO$_2$H | 3 | 123–134 | Calcd for C$_{32}$H$_{36}$N$_4$O$_{10}$<br>C, 60.37; H, 5.70; N, 8.80<br>Found: C, 60.11; H, 5.82; N, 8.76. |
| 87 | CN | 3 | 141–151 | Calcd for C$_{31}$H$_{33}$N$_5$O$_8$.1.5H$_2$O:<br>C, 59.04; H, 5.75; N, 11.10<br>Found: C, 59.27; H, 5.72; N, 11.42. |

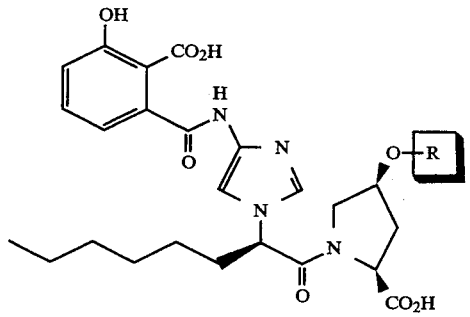

| Example | R | Yield (%) | M.P. (°C.) | Elemental Analysis |
|---|---|---|---|---|
| 88 | (indane) | 9 | 148–153 | Calcd for C$_{33}$H$_{38}$N$_4$O$_8$.0.75HCl:<br>C, 61.35; H, 6.05; N, 8.67<br>Found: C, 61.30; H, 6.01; N, 8.64. |
| 89 | (naphthalene) | 2 | 146–152 | Calcd for C$_{34}$H$_{36}$N$_4$O$_8$.0.5H$_2$O:<br>C, 64.04; H, 5.84; N, 8.78<br>Found: C, 63.98; H, 5.77; N, 8.65 |

| Example | R | Yield (%) | M.P. (°C.) | Elemental Analysis |
|---------|---|-----------|------------|---------------------|
| 90 | (dimethoxyphenyl, with OCH₃ groups) | 4 | 130–135 | Calcd for $C_{32}H_{38}N_4O_{10}$: C, 58.52; H, 6.13; N, 8.53 Found: C, 58.30; H, 5.98; N, 8.40 |

Example 91

1-[1-oxo-2-[4-(2-sulfobenzoyl)amino-1H-imidazol-1-yl]octyl]-4-cis-(4-methyleneophosphonic acid)-phenoxy)-L-proline To a solution of dimethylphosphite (22.4 mL, 244 mmol) in 400 mL of anhydrous THF at 0° C. was added NaH (9.3 g, 232 mmol, 60% dispersion in mineral oil) in small portions. Benzyloxybenzylchloride (53.7 g, 232 mmol) was then introduced via canula as a solution in 100 mL of anhydrous THF. The resulting mixture was warmed to room temperature and stirred overnight. The solvent was then removed in vacuo and the resulting oil was partitioned between H₂O/ether (300 mL ea.). The layers were separated, and the aqueous extracted with ether (2×200 mL). The organic was combined, dried (Na₂SO₄) and concentrated to give 78 g of a thick oil. Chromatography (SiO₂, 75% ethyl acetate/25% hexane) provided 36.6 g (52%) of dimethyl-(4-benzyloxy)benzylphosphonate as a solid residue. (MS).

Calculated for $C_{16}H_{19}O_4P$: C, 62.74; H, 6.25. Found: C, 62.96; H, 6.23.

A solution of dimethyl-(4-benzyloxy)-benzylphosphonate (19.4 g, 63 mmol) in 100 mL of 1% con. HCl in ethanol was treated with 840 mg of 5% Pd/C. The mixture was hydrogenated at 40 psi for 30 minutes The reaction mixture was then filtered through a pad of celite, and the filtrate concentrated in vacuo to give 13.6 g (100 %) of dimethyl-(4-hydroxy)-benzylphosphonate as a white solid. M.pt. 126°–129° C.

Calculated for $C_9H_{13}O_4P$: C, 50.01; H, 6.06. Found: C, 50.21; H, 6.09.

To a solution of N-carbobentyloxy-trans-4-hydroxy-proline methyl ester (10.0 g, 35.8 mmol) in 400 mL of anhydrous THF under N₂ at 0° C. was added triphenylphosphine (10.6 g, 39.4 mmol) and dimethyl-(4-hydroxy)-benzylphosphonate (7.9 g, 37.8 mmol). To this mixture was added diethyl azodicarboxylate (6.3 mL, 39.4 mmol) dropwise over a 30 minute period. The reaction mixture was then allowed to warm to room temperature and stirred for 18 hours. The solvent was then removed in vacuo and the residue was chromatographed (SiO₂, 50–100% ethyl acetate/hexane) to give 13.3 g (75%) of N-carbobenzyloxy-4-(cis)-(dimethyl-4-oxobenzyl phosphonate)-L-proline methyl ester as a thick oil.

Calculated for $C_{23}H_{28}NO_8P$: C, 57.86; H, 5.91; N, 2.93. Found: C, 57.66; H, 6.04; N, 3.02.

A solution of N-carbobenzyloxy-4-(cis)-(dimethy-4-oxobenzylphosphonate)-L-proline methyl ester (6.6 g, 13.8 mmol) in 100 mL of 1% concentrated HCl in ethanol was treated with 1.0 g of 10% Pd/C. The mixture was hydrogenated at 40 psi for 2 hours and then passed through a pad of celite to remove the catalyst. The filtrate was concentrated to an oil and then partitioned between CHCl₃ and saturated NaHCO₃ (100 mL each). The layers were separated and the organic was dried (Na₂SO₄), and concentrated in vacuo to give the crude deprotected proline ester as a pale yellow oil.

In a separate flask, 2-(4-nitroimidazole)-octanoic acid (3.7 g, 14.5 mmol) was dissolved in 25 mL of anhydrous CH₂Cl₂. To this solution was added oxalyl chloride (1.7 mL, 18.9 mmol) followed by 3 drops of DMF. When gas evolution ceased, the solvent was removed in vacuo to give the acid chloride as an amber oil that was evaporated from an additional 20 mL of CH₂Cl₂. The acid chloride was used immediately in the next reaction.

To a solution of the above proline ester in 20 mL of anhydrous CH₂Cl₂ at 10° C. was added N,N-diisopropylethylamine (2.7 mL, 15.1 mmol). The acid chloride was then introduced dropwise from an addition funnel as a solution in 10 mL of CH₂Cl₂. The resulting mixture was warmed to room temperature and stirred for 18 hours. The reaction was next distributed between ethyl acetate/H₂O (200 mL ea.). The layers were separated and the aqueous extracted with ethyl acetate (3×100 mL). The organic was combined and washed with brine followed by H₂O. The organic was then dried (Na₂SO₄) and concentrated in vacuo to give as 1-[1-oxo-2-(4-nitro-1H-imidazol-1-yl)octyl]-4-cis-[(4-dimethylmethylenephosphonate)-phenoxy]-L-proline methyl ester an oil. The diastereomeric octanoamides were separated by chromatography (SiO₂, 1% methanol/ethyl acetate to give 1.57 g (19%) of the (R,S,S) isomer and 1.225 g of the (S,S,S) isomer along with 1.12 g of a mixed fraction. Data for (R,S,S) isomer: (MS).

Calculated for $C_{26}H_{37}N_4O_9P$: C, 53.79; H, 6.42; N, 9.65 Found: C, 53.26; H, 6.58; N, 9.18.

Data for (S,S,S) isomer: (MS) Calculated for $C_{26}H_{37}N_4O_9P$: C, 53.79; H, 6.42; N, 9.65 Found: C, 53.55; H, 6.47; N, 9.38.

To a solution of 4-nitroimidazole octanoamide (4.0 g, 6.9 mmol) in 50 mL of absolute ethanol was added 1.0 g of 5% Pd/C. The mixture was hydrogenated at 40 psi for 30 minutes. The catalyst was then removed by passing the mixture through a pad of celite. The filtrate was concentrated to an amber oil that was azeotroped 2× from anhydrous THF.

In a separate flask, sulfobenzioc anhydride (1.4 g, 7.6 mmol) was dissolved in 5 mL of anhydrous THF under N₂. To this solution was added the above aminoimidazole as a solution in 5 mL of anhydrous THF. After stirring for 30 minutes, the solution was triturated with ether/hexanes to yield 4.70 g (93%) of the sulfonic acid as a light yellow solid that was collected by filtration. This product, 1-[1-oxo-2-[4-(2-sulfobenzoyl)amino-1H-imidazol-1-yl]octyl]-4-cis-[(4-dimethylmethylenephosphonate)-phenoxy]-L-proline methyl ester, was used in the next reaction without further purification. M.pt. 110° C. (decomp). (MS).

Calculated for $C_{33}H_{43}N_4O_{11}PS$: C, 53.94; H, 5.90; N, 7.62 Found: C, 53.66; H, 5.94; N, 6.85.

To a solution of the above methyl ester (4.70 g, 6.5 mmol) in 25 mL of anhydrous CH₂Cl₂ at 0° C. was added trimethylsilylbromide (5.0 g, 32.4 mmol) dropwise over a 15 minute period. The resulting mixture was warmed to room temperature and stirred for 1 hour. The solvent was then removed in vacuo, and the residue dissolved in 16 mL of 2N NaOH. After stirring for 1 hour, the reaction mixture was acidified to pH=1.0 with 5N HCl. The aqueous was extracted with 10% ethanol/ethyl acetate (3×50 mL). The organic was dried (Na$_2$SO$_4$) and concentrated to give a solid residue that was dissolved in minimal absolute ethanol and triturated with ether/hexanes. Isolation by filtration provided 2.79 g (61%) of the title phosphonic acid as a pale yellow solid. M.pt. 190° C. (decomp). (MS).

Calculated for C$_{30}$H$_{37}$N$_4$O$_{11}$PS: C, 52.02; H, 5.38; N, 8.09 Found: C, 51.80; H, 5.42; N, 7.91.

Example 92

1 -[1-oxo-2-[4-(2-sulfobenzoyl)amino-1H-imidazol-1-yl]octyl]-4-cis-[(4-N-methanesulfonamido)-phenoxy]-L-proline.

To a solution of N-Boc-trans-4-hydroxyproline methyl ester (10.0 g, 41 mmol) 150 mL of anhydrous THF at 0° C. under N$_2$ was added triphenylphosphine (12.7 g, 48 mmol) and 4-nitrophenol (6.7 g, 48 mmol). To this mixture was added diethylazodicarboxylate (7.7 mL, 48 mmol) dropwise over a 30 minute period. The mixture was warmed to room temperature. After stirring for 2 days, the solvent was removed in vacuo, and the crude oil treated successively with 200 mL portions of toluene and ether to remove triphenylphosphine oxide and diethylazodihydrazide by crystallization. The resulting oil was then chromatographed (SiO$_2$, 15–50% ethyl acetate/hexanes) to provide 5.2 g (34%) of N-Boc-4-(cis)-(4-nitrophenoxy)-L-proline methyl ester as a light yellow oil.

Calculated for C$_{17}$H$_{22}$N$_2$O$_7$: C, 55.73; H, 6.05; N, 7.65 Found: C, 55.94; H, 6.09; N, 7.59.

To a solution of N-Boc-4-(cis)-(4-nitrophenoxy)-L-proline methyl ester (9.0 g, 24.7 mmol) in 100 mL of ethanol was added 1.5 g of 10% Pd/C. This mixture was hydrogenated for 3 hours at 40 psi. The catalyst was then removed by passing the reaction through a pad of celite. Concentration in vacuo gave an oil that was used immediately in the next reaction.

The above oil was dissolved in 50 mL of anhydrous CH$_2$Cl$_2$ along with 11.5 mL (65.5 mmol) of N,N-diisopropylethylamine. To this mixture was added methanesulfonyl chloride (6.4 g, 55 mmol) dropwise via an addition funnel as a solution in 10 mL of CH$_2$Cl$_2$. After stirring for 2 hours, the reaction was poured into H$_2$O (200 mL). The aqueous was extracted with ethyl acetate (3×100 mL). The organic was dried (Na$_2$SO$_4$) and concentrated in vacuo to an oil. Chromatography (SiO$_2$, 25% ethyl acetate/hexanes) provided 3.22 g (27%) of N-Boc-4-(cis)-((4-N,N-bismethanesulfonamido)-phenoxy)-L-proline methyl ester as a colorless oil.

Calculated for C$_{19}$H$_{28}$N$_2$O$_9$S$_2$: C, 46.33; H, 5.73; N, 5.69 Found: C, 46.16; H, 5.48; N, 5.45.

To a solution of N-Boc-4-(cis)-[(4-N,N-bismethanesulfonamido)-phenoxy]-L-proline methyl ester (3.0 g, 6.1 mmol) in 40 mL of anhydrous CH$_2$Cl$_2$ at room temperature was added trifluoroacetic acid (1.5 mL, 18 mmol). After stirring for 3 hours, the solvent was removed in vacuo to give an oil that was partitioned between saturated NaHCO$_3$ solution and ethyl acetate (100 mL ea.). The organic was dried (Na$_2$SO$_4$) and concentrated to yield 2.27 g (94%) of 4-(cis)-[(4-N,N-bismethanesulfonamido)phenoxy]-L-proline methyl ester as a solid that was used immediately in the next reaction.

2-(4-Nitroimidazole)-octanoic acid (1.7 g, 6.7 mmol) was converted to the acid chloride and reacted with the above proline ester using the previously described method. Chromatography (SiO$_2$, 70–100% ethyl acetate/hexanes) of the crude reaction mixture provided 1.66 g (43%) of the (R)-1-[1-oxo-2-(4-nitro-1H-imidazol-1-yl)octyl]-4-(cis)-[(4-N,N-bismethanesulfonamido)-phenoxy]-L-proline methyl ester as a white solid. M.Pt. 106–109.

Calculated for C$_{25}$H$_{35}$N$_5$O$_{10}$S$_2$: C, 47.69; H, 5.60; N, 11.12 Found: C, 47.88; H, 5.51; N, 11.22.

To a solution of (R)-1-[1-oxo-2-(4-nitro-1H-imidazol-1-yl}octyl]-4-(cis)-[{4-N,N-bismethanesulfonamido-phenoxy]-L-proline methyl ester (1.26 g, 2.0 mmol) in 50 mL of absolute ethanol was added 0.5 g of 5% Pd/C. The mixture was hydrogenated at 40 psi for 1.5 hours. The catalyst was then removed by passing the mixture through a pad of celite. The filtrate was concentrated to an amber oil that was azeotroped 2× from anhydrous THF.

In a separate flask, sulfobenzioc anhydride (0.40 g, 2.2 mmol) was dissolved in 5 mL of anhydrous THF under N$_2$. To this solution was added the above aminoimidazole as a solution in 5 mL of anhydrous THF. After stirring for 30 minutes, the solution was triturated with ether/hexanes to yield 1.50 g (95%) of (R)-1-[1-oxo-2-[4-(2sulfobenzoyl)amino-1H-imidazol-1-yl)octyl]-4-(cis)-[(4-N,N-bismethanesulfonamido)-phenoxy]-L-proline methyl ester, as a light yellow solid that was collected by filtration. This intermediate was used in the next reaction without further purification. M.P. 165°–170° C. (MS).

Calculated for C$_{32}$H$_{41}$N$_5$O$_{12}$S$_3$.1.0 H$_2$O: C, 47.93; H, 5.40; N, 8.73. Found: C, 48.31; H, 5.40; N, 8.44.

(R)-1-[1-Oxo-2-[4-(2-sulfobenzoyl)amino-1H-imidazol-1-yl]octyl]-4-(cis)-[(4-N,N-bismethanesulfonamido)-phenoxy]-L-proline methyl ester (0.40 g, 0.52 mmol) was dissolved in a solution of 1N NaOH (3 mL) and THF (2 mL) at room temperature. The solution was stirred overnight. The pH was then adjusted to 1.0 with 1N HCl. A precipitate formed that was extracted from the aqueous using 10% ethanol/ethyl acetate. Drying (Na$_2$SO$_4$) and concentration in vacuo gave a solid residue that was triturated from MeOH/ether to yield 0.27 g (75%) of (R)-1-[1-oxo-2-[4-(2-sulfobenzoyl)amino-1H-imidazol-1-yl)octyl]-4-(cis)-((4-N-methansulfonamido)-phenoxy)-L-proline as a white solid. M.pt. 195°–198° C. MS.

Calculated for C$_{30}$H$_{37}$N$_5$O$_{10}$S$_2$: C, 52.09; H, 5.39; N, 10.12. Found: C, 51.82; H, 5.47; N, 10.28.

Example 93

(R)-1-[1-oxo-2-[4-(2-sulfobenzoyl)amino-1H-imidazol-1-yl]octyl]-4-(cis)-((4-N-triflouromethanesulfonamido)-phenoxy)-L-proline Prepared in a manner analogous to Example 92 was (R)-1-[1-oxo-2-[4-(2-sulfobenzoyl)amino-1H-imidazol-1-yl]octyl]-4-(cis)-((4-N-triflouromethanesulfonamido)-phenoxy)-L-proline. MP 145° C. (dec). MS.

Calculated for C$_{30}$H$_{33}$N$_5$O$_{10}$S$_2$F$_3$.1.0 NaCl: C, 46.93; H, 4.84; N, 9.99. Found: C, 46.97; H, 4.58; N, 9.75.

Example 94

(R)-1-[1-oxo-2-[4- (2-sulfobenzoyl)amino-1H-imidazol-1-yl]octyl]-4-(cis)-[(4-N,N-methyl-methanesulfonamido)phenoxy]-L-proline.

To a solution of 4-benzyloxyaniline (21.7 g, 108 mmol) in 100mL of anhydrous CH$_2$Cl$_2$ was added N,N-diisopropylethylamine (31.0, 42.5 mmol). The mixture was then cooled to 10° C. and treated with methanesulfonylchloride (18.2 mL, 234 mmol). After stirring for 1 hour, the reaction was distributed between H₂O/ethyl acetate. A solid formed that was collected by filtration. Drying in vacuo provided 25.7 g (68%) of 4-benzyloxy-N,N-bismethansulfonamido-benzene as a brown solid. M.Pt. 212°–215° C. MS.

Calculated for C₁₅H₁₇NO₅S₂: C, 50.69; H, 4.82; N, 3.94. Found: C, 50.87; H, 4.85; N, 3.91.

To a solution of 4-benzyloxy-N,N-bismethansulfonamidobenzene (25.0 g, 71.0 mmol) in 300 mL of THF was added 1N NaOH (250 mL). The resulting solution was stirred for 2 hours at 70° C. Upon cooling, the mixture was acidified to pH=1.0 with 5N HCl. Extraction with CHCl₃ (5×250 mL), followed by drying (Na₂SO₄) and concentration in vacuo provided 15.05 g (51%) of 4-benzyloxy-N-methansulfonamidobenzene as a white solid. M.Pt. 155°–158° C. MS.

Calculated for C₁₄H₁₅NO₃S: C, 60.63; H, 5.45; N, 5.05. Found: C, 60.59; H, 5.46; N, 5.01.

To a solution of the above compound (15.0 g, 55.0 mmol) in 45 mL of anhydrous DMF was added K₂CO₃ (15.3 g, mmol). To this mixture was added MeI (11.8 g, 83.0 mmol). After stirring at room temperature for 18 h a precipitate formed that was collected by first diluting the reaction with H₂O, following by vacuum filtration. Drying in vacuo yielded 15.7 g (97%) of 4-benzyloxy-N,N-methylmethanesulfonamido-benzene as a white solid. M.Pt. 175°–178° C . MS.

Calculated for C₁₅H₁₇NO₃S: C, 61.83; H, 5.88; N, 4.81. Found: C, 62.04; H, 5.96; N, 4.97.

To a solution of 4-benzyloxy-N,N-methylmethanesulfonamido-benzene (14.0 g, 48 mmol) in 100 mL of ethanol was added 4.0 g of 5 % Pd/C. The mixture was hydrogenated at 40 psi for 2 hours. The reaction was then passed through a pad of celite, and the filtrate concentrated to give 9.93 g (100%) of 4-N,N-methylmethanesulfonamidophenol as a white solid. M.pt. 117°–120° C. MS.

Calculated for C₈H₁₁NO₃S: C, 47.75; H, 5.51; N, 6.96. Found: C, 47.65; H, 5.28; N, 6.88.

This material was employed analogous to Example 92 to prepare the titled compound.

Example 95

(R)-1-[1-oxo-2-[4-(2-sulfobenzoyl)amino-1H-imidazol-1-yl]octyl]-4-(cis)-[(4-(methylene-N-methanesulfonamido))phenoxyl-L-proline.

To a solution of N-carbobenzyloxy-trans-4-hydroxy-L-proline methyl ester (10.0 g, 35.8 mmol) in 200 mL of anhydrous THF under N₂ was added triphenylphosphine (10.6 g, 39.4 mmol) and 4 -cyanophenol ( 4.7 g, 39.4 mmol). This solution was cooled to 0° C. and then treated with diethylazodicarboxylate (6.3 mL, 39.4 mmol), added dropwise over 30 minutes The reaction was warmed to room temperature and stirred for 2 days. The solvent was removed in vacuo and the residue chromatographed (SiO₂, 30% ethyl acetate/hexanes) to provide 12.1 g (89%) of N-carbobenzyloxy-4-(cis)-(4-cyanophenoxy)-L-proline methyl ester as a colorless oil. MS.

Calculated for C₂₁H₂₀N₂O₅: C, 66.31; H, 5.30; N, 7.36. Found: C, 66.10; H, 5.34; N, 7.50.

To a solution of N-carbobenzyloxy-4-(cis)-(4-cyanophenoxy)-L-proline methyl ester (3.8 g, 10 mmol) in 75 mL of methanol was added COCl₂ (2.6 g, 20 mmol). This solution was cooled to 0° C. and then treated with NaBH₄ (3.8 g, 100 mmol), added in small portions. After stirring for 2 hours, 50 mL of 3N HCl were added. After stirring this solution for 15 minutes, the reaction was distributed between H₂O/ether (200 mL ea.). The layers were separated, and the aqueous phase was extracted with ether (2×100 mL). The aqueous was then made basic with concentrated NH₄OH solution. Extraction with ethyl acetate (3×100 mL), followed by drying (Na₂SO₄) and concentration in vacuo provided 3.50 g (90%) of N-carbobenzyloxy-4-(cis)-[(4-aminomethyl)-phenoxy]-L-proline methyl ester as an oil. This material was used in the next reaction without further purification. MS.

Calculated for C₂₁H₂₄N₂O₅: C, 65.61; H, 6.29; N, 7.29. Found: C, 65.87; H, 6.04; N, 7.03.

To a solution of N-carbobenzyloxy-4-(cis)-[(4-aminomethyl)-phenoxy]-L-proline methyl ester (0.90 g, 2.34 mmol) in 15 mL of anhydrous CH₂Cl₂ was added N,N-diisopropylamine (0.6 mL, 3.4 mmol). This solution was cooled to 0° C. and then treated with methanesulfonylchloride (0.22 mL, 2.8 mmol), added as a solution in 5 mL of CH₂Cl₂. After stirring for 1.5 hours, the reaction was distributed between ethyl acetate/H₂O (50 mL ea.). The layers were separated , and the aqueous was extracted with ethyl acetate (2×50 mL). The organic was dried (Na₂SO₄) and concentrated in vacuo to give a crude oil. Chromatography (SiO₂, 50/50 ethyl acetate/hexanes) provided 0.74 g (70%) of N-carbobenzyloxy-4-(cis }-[(4-(methylene-N-methanesulfonamido))-phenoxy]-L-proline methyl ester as a colorless oil. MS.

To a solution of (−)-cinchonidine (48.0 g, 163 mmol) in 880 mL of distilled H₂O at room temperature was added 2-(4-nitro-1H-imidazol-1-yl)-octanoic acid (83.0 g, 326 mmol) as a solution in 440 mL of ethanol. To this mixture was added triethylamine (11.7 mL). The mixture was then heated to 80° C., and the pH was maintained between 6.9 and 7.1 by the dropwise addition of triethylamine (5–10 mL). After the pH stabilized at 7.01, the solution was allowed to cool to room temperature, and let stand overnight whereupon crystallization of the (R)-2-(4-nitro-1H-imidazol-1-yl)octanoic acid-cinchonidine salt occurred. The crystalline salt was collected by filtration. The salt was then suspended in 200 mL ea. of ethyl acetate/H₂O. To this suspension was added 1N HCl (750 mL). The layers were separated, and the aqueous was extracted with ethyl acetate (2×500 mL). The organic was combined, dried (Na₂SO₄), and concentrated in vacuo to provide 29.9 g (72%) of (R)-2-(4-nitro-1H-imidazol-1-yl)-octanoic acid as an off-white solid. M.pt. 116°–118° C.

Calculated for C₁₁H₁₇N₃O₄: C, 51.76; H, 6.71; N, 16.46. Found: C, 51.89; H, 6.76; N, 16.20. [α]_D −29.9 (c1.00, ethanol).

Enantiomeric excess was determined to be 96% by conversion of the acid to its methyl ester (diazomethane), followed by HPLC analysis employing a chiral column.

(R)-2-(4-Nitro-1H-imidazol-1-yl)-octanoic acid (16.0 g, 63.0 mmol) was dissolved in 1 L of anhydrous methanol. To this solution was added pTsOH (300 mg). The reaction was then heated to reflux for 16 hours. Upon cooling, the solvent was removed in vacuo, to give an oil that was dissolved in 300 mL of ethyl acetate. The solution was washed (2×250 mL) with saturated NaHCO₃ solution. The organic was then dried (Na₂SO₄) and concentrated in vacuo to provide 13.2 g (78%) of (R)-methyl-2-(4-nitro-1H-imidazol-1-yl)-octanoate as an amber oil.

Calculated for $C_{12}H_{19}N_3O_4$: C, 53.32; H, 7.11; N, 15.60. Found: C, 53.23; H, 7.05; N, 15.39.

(R)-Methyl-2-(4-nitro-1H-imidazol-1-yl)-octanoate (13.0 g, 45.7 mmol) was dissolved in 150 mL of absolute ethanol. To this solution was added 2.0 g of 10% Pd/C. The mixture was hydrogenated at 40 psi for 2 hours. The catalyst was then removed by passing the reaction through a pad of celite. The filtrate was then concentrated to an oil that was evaporated twice from anhydrous THF (100 mL). The crude product was then dissolved in 100 mL of anhydrous THF and treated with KOAc (4.44 g) and $K_2CO_3$ (3.12 g). To this mixture was added sulfobenzoic anhydride (8.83 g, 47.7 mmol). The reaction was stirred for 4 hours after which time a precipitate formed. The mixture was diluted with THF (100 mL) and the solid collected by filtration. Drying in vacuo provided 22.5 g of crude (R)-methyl-[(2-sulfobenzoyl)amino-1H-imidazol-1-yl]-octanoate-potassium salt. This material was carried on to the next reaction without further purification.

The potassium salt (22.5 g) was dissolved in a mixture of 200 mL $H_2O$ and 100 mL of ethanol. To this solution was added 1N NaOH (53 mL). The reaction was allowed to stir for 3 hours. Ethanol was then removed in vacuo, and the aqueous acidified to pH=1.5 with 5N HCl. This solution was extracted with 10% ethanol/ethyl acetate ($\times 200$ mL). The organic was dried ($Na_2SO_4$) and concentrated in vacuo to give 8.65 g (46% for two steps) of (R)-[(2sulfobenzoyl)amino-1H-imidazol-1-yl]-octanoic acid as a white solid. MS.

Calculated for $C_{18}H_{23}N_3O_6S$: C, 52.80; H, 5.66; N, 10.26. Found: C, 52.53; H, 5.59; N, 10.27.

To a solution of N-carbobenzyloxy-4-(cis)-[(4(methylene-N-methanesulfonamide))-phenoxy]-L-proline methyl ester (1.5 g, 3.25 mmol) in 50 mL of absolute ethanol was added 0.5 g of 5% Pd/C. This mixture was hydrogenated at 40 psi for 1.5 hours. The reaction mixture was then passed through a pad of celite, and the filtrate concentrated in vacuo to give 1.07 g of 4-(cis)-[(4-(methylene-N-methanesulfonamido))-phenoxy]-L-proline methyl ester as an oil. MS. This material was used immediately in the next reaction.

To a solution of the above amine in 10 mL of anhydrous DMF was added (R)-[(2-sulfobenzoyl)amino-1H-imidazol-1-yl]-octanoic acid (1.00 g, 2.45 mmol) and hydroxybenzotriazole (0.37 g, 2.77 mmol). This mixture was cooled to 0° C., and then treated with dicyclohexylcarbodiimide (0.56 g, 2.70 mmol). The resulting solution was warmed to room temperature and stirred for 48 hours. After removal of dicyclohexylurea by filtration, the filtrate was diluted with 100 mL of ethyl acetate and washed several times with $H_2O$. The organic was then dried ($Na_2SO_4$) and concentrated in vacuo to an oil. Chromatography ($SiO_2$, 5% methanol/$CHCl_3$) provided 0.84 g (34%) of (R)-1-[1-oxo-2-[4-(2-sulfobenzoyl)amino-1H-imidazol-1-yl]octyl]-4-(cis)-[(4-(methylene-N-methanesulfonamido))-phenoxy]-L-proline methyl ester as a white solid. M. pt. 150 (dec).

Calculated for $C_{32}H_{41}N_5O_{10}S_2$: C, 53.40; H, 5.74; N, 9.73. Found: C, 53.66; H, 5.97; N, 9.50.

R) -1-[1-oxo-2-[4-(2-sulfobenzoyl)amino-1H-imidazol-1-yl]octyl]-4-(cis)-[(4-(methylene-N-methanesulfonamido))phenoxy]-L-proline methyl ester (0.37 g, 0.52 mmol) was dissolved in a mixture of 1N NaOH (3.0 mL) and THF (7 mL). This solution was stirred for 1 hour. The THF was then removed in vacuo, and the aqueous was acidified to pH=1.0 using 1N HCl. Extraction with 5% ethanol/ethyl acetate ($2\times$) followed by drying ($Na_2SO_4$) of the organic and concentration yielded a solid residue. Trituration from ethanol/ethyl acetate-ether provided 0.26 g (74%) of (R)-1-[1-oxo-2-[4-(2-sulfobenzoyl)amino-1H-imidazol-1-yl]octyl]-4-(cis)-[(4-(methylene-N-methanesulfonamido))-phenoxy]-L-proline as an off-white solid. M.pt. 172-176.

Calculated for $C_{31}H_{39}N_5O_{10}S_2$: C, 52.75; H, 5.57; N, 9.92. Found: C, 52.54; H, 5.53; N, 10.15.

As previously discussed, the compounds of Formula I are potent effective antagonists of angiotensin II. The ability of representative compounds of Formula I to block angiotensin II receptor binding was determined using the adrenal glomerulosa assay. The ability to antagonize angiotensin-induced vasoconstriction was evaluated in the rabbit aorta test system.

Adrenal Glomerulosa Test System

Binding of $I^{125}$-angiotensin II to adrenal membranes was routinely carried out in 96-well filtration plates. Adrenal membranes were prepared from the capsular portion (glomerulosal layer attached) of rat adrenal glands by differential centrifugation. Briefly, capsules were homogenized in a solution containing sucrose, 250 mM; $MgCl_2$, 1 mM; and tris, 5 mM at pH 7.5 and 4° C. using a polytron at setting 5 for 20 seconds. The homogenate was stirred, gently, for 15 minutes at 4° C. and then centrifuged 10 minutes, at $1000\times g$, 4° C. The supernatant was centrifuged 30 minutes, at $30,000\times g$, 4° C., and the resulting pellet resuspended in 50 mM tris. Membrane preparations were stored in aliquots at $-70$° C. until used. Binding of $I^{125}$-angiotensin II to adrenal membranes was performed at room temperature for 90 minutes in 96-well plates containing a hydrophilic polyvinylidene fluoride membrane (0.45 μm, Millipore-GV multiscreen). Each 250 μl incubate contained the following (final concentration): tris, 50 mM; NaCl, 120 mM; $MgCl_2$, 5mM; dithiothrietol 1 mM; bovine serum albumin, 0.05%; $I^{125}$-angiotensin II, 0.1 nM; and adrenal membrane protein, 8–15 μg. Antagonists were added in concentrations from 10 nM to 100 μM. Non-specific binding was measured in the presence of 0.1 μM Sar$_1$, Ile$_8$ angiotensin II.

Binding was terminated by vacuum filtration. Receptor-ligand complex trapped on filters was washed 3 times with 300 μl ice-cold wash solution (tris, 50 mM; NaCl, 120 mM; $MgCl_2$, 5 mM; dithiothrietol, 1 mM). Filter discs were dried, punched out and counted in a gamma counter at 52% efficiency. Specific binding represented 96% of total binding (approximately 150 fmol angiotensin II/mg protein). The molar concentration ($IC_{50}$) of the inhibitor that displaced 50% of the binding of $I^{125}$ angiotensin II for each compound was calculated using a 4 parameter logistics model (NonLin, SAS Institute). Data are expressed as $K_I$ calculated using the Cheng Prusoff equation. See Cheng et al. *Biochem. Pharmacol.* 22: 3099 (1973).

Rabbit Aorta Test System

New Zealand white rabbits (Hazelton, 2–3 kg) were sacrificed by cervical dislocation. The thoracic aortas were removed and cleaned of excess fat and connective tissue. Rings of tissue (3 mm wide) were mounted in 10 ml tissue baths between 2 L-shaped stainless steel hooks. The lower hook was attached to a stationary rod. The upper hook was attached to a force displacement transducer (Grass model FT.03). The bath chambers were maintained at 37° C., aerated with 95% $O_2$/5% $CO_2$, and contained physiological solution of the following composition (mM): NaCl, 117; glucose, 5.6; NaH$_2$PO$_4$, 1.0; MgSO$_4$, 0.7; KCl, 5.2; CaCl$_2$, 1.8; NaHCO$_3$, 26; and phentolamine HCl, 0.003.

Rings were equilibrated for 1 hour with 2 g of tension. During the equilibration period, the tissues were washed by overflow every 15 minutes. Rings were then exposed to 10$^{-8}$M angiotensin II (AII) and were allowed to contract until a steady state was reached. Tissues were then washed every 15 minutes for 1 hour. This was repeated every hour until the AII response stabilized. A cumulative concentration response curve to AII (10$^{-10}$ to 10$^{-7}$M) was then obtained. At the conclusion of the concentration response curve, tissues were washed every 2 minutes until baseline tension was reached, then every 15 minutes for 30 minutes. Compounds were added in a volume of 10 $\mu$l DMSO and allowed to incubate for 30 minutes before repeating the concentration response curve to AII. Contractions to AII were expressed as a percent of the maximum contraction obtained in the control curve (the first AII concentration response curve). EC$_{50}$'s (concentration that contracted the tissues to $\frac{1}{2}$ the control maximum) for each curve were calculated using a 4 parameter logistics model (NonLin, SAS Institute). Potency data for each compound tested are expressed as the pA$_2$ (defined as $-\log K_B$, where $K_B$=[molar concentration of antagonist]/[(EC$_{50}$ AII with antagonist/EC$_{50}$ AII without antagonist)-1]).

Using the methology described, representative compounds of the present invention were evaluated and were found to exhibit activity as measured by a PA$_2$ of at least 4.1 using the rabbit aorta test system thereby demonstrating and confirming the utility of the compounds of the invention as effective angiotensin II antagonists.

TABLE 1

| Example | Adrenal Glomulosa (K$_I$, $\mu$m) | Rabbit Aorta (pA$_2$) |
| --- | --- | --- |
| 1 | 10.3 | 5.7 |
| 2 | 8.2 | 6.1 |
| 3 | 9.6 | 5.4 |
| 4 | 12.1 | 6.0 |
| 5 | 178 | 6.3 |
| 6 | * | 6.3 |
| 7 | 6.8 | 5.8 |
| 8 | 13.0 | 5.8 |
| 9 | 12.4 | 6.6 |
| 10 | 2.93 | 7.2 |
| 11 | * | 6.7 |
|   | * | 6.6 |
| 12 | * | 9.2 |
|   | * | 8.2 |
| 13 | * | 7.2 |
|   | * | 6.9 |
| 14 | * | 7.5 |
|   | * | 6.9 |
| 15 | * | 8.5 |
|   | * | 7.2 |
| 16 | * | 7.3 |
| 17 | * | 7.8 |
| 18 | * | 9.7 |
| 19 | * | 8.9 |
| 20 | * | 8.5 |
| 21 | * | 7.2 |
|   | * | 6.3 |
| 22 | * | 9.4 |
| 23 | * | 8.8 |
| 24 | * | 7.6 |
| 25 | * | 6.9 |
| 26 | * | 8.6 |
| 27 | * | 8.0 |
| 28 | * | 8.7 |
| 29 | * | 7.5 |
| 30 | * | 9.2 |
| 31 | * | 8.9 |
| 32 | * | 8.9 |
| 33 | * | 9.0 |
| 34 | * | 8.5 |
| 35 | * | 8.7 |
| 36 | * | 9.4 |
| 37 | * | 9.4 |
| 38 | * | 8.9 |
| 39 | * | 9.0 |
| 40 | * | 9.3 |
| 41 | * | 9.8 |
| 42 | * | 8.9 |
| 43 | * | 9.1 |
| 44 | * | 8.3 |
| 45 | * | 9.6 |
| 46 | * | 8.7 |
| 47 | * | 9.0 |
| 48 | * | 9.2 |
| 49 | * | 8.6 |
| 50 | * | 8.7 |
| 51 | * | 7.9 |
| 52 | * | 8.4 |
| 53 | * | 8.0 |
| 54 | * | 8.6 |
| 55 | * | 9.4 |
| 56 | * | 7.5 |
| 57 | * | 9.5 |
| 58 | * | 9.1 |
| 59 | * | 9.2 |
| 60 | * | 7.8 |
| 61 | * | 8.5 |
| 62 | * | 9.0 |
| 63 | * | 8.8 |
| 64 | * | 5.7 |
| 65 | * | 8.7 |
| 66 | * | 8.2 |
| 67 | * | 8.2 |
| 68 | * | 9.3 |
| 69 | * | 9.3 |
| 70 | * | 9.3 |
| 71 | * | 7.6 |
| 72 | * | 8.5 |
| 73 | * | 6.8 |
| 74 | * | 7.0 |
| 75 | * | 9.0 |
| 76 | * | 7.5 |
| 77 | * | 8.8 |
| 78 | * | 8.5 |
| 79 | * | 9.3 |
| 80 | * | 8.1 |
| 81 | * | 8.8 |
| 82 | * | 9.5 |
| 83 | * | 8.9 |
| 84 | * | 8.0 |
| 85 | * | 8.9 |
| 86 | * | 9.1 |
| 87 | * | 7.5 |
| 88 | * | 8.2 |
| 89 | * | 7.5 |
| 90 | * | 7.7 |
| 91 | * | 10.1 |
| 92 | * | 9.9 |
| 93 | * | 8.9 |
| 94 | * | 9.6 |
| 95 | * | 9.8 |

*indicates data are not available

The term "pharmaceutically effective amount", as used herein, represents an amount of a compound of the invention which is capable of blocking angiotensin II receptors in mammals. The particular dose of the compound administered according to this invention will, of course, be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical daily dose will contain from about 0.01 mg/kg to about 20 mg/kg of the active compound of this invention. Preferred daily doses will be about 0.05 to about 10 mg/kg, ideally about 0.1 to about 5 mg/kg. The term "treating," as used herein, describes the management and care of a patient for the purpose of combating the disease, condition, or disorder.

The term "treating" includes the administration of a compound of present invention to prevent the onset of the symptoms, alleviating the symptoms, or eliminating the disease, condition, or disorder.

The term "enhancing cognitive performance," as used herein, describes facilitating memory and learning in patients in need of such treatment. Examples include patients suffering from cognitive impairments like age associated mental impairment and Alzheimer's disease.

The compounds of Formula I are preferably formulated prior to administration. Therefore, yet another embodiment of the present invention is a pharmaceutical formulation comprising a compound of Formula I and one or more pharmaceutically acceptable carriers, diluents or excipients therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

| | Quantity (mg/capsule) |
|---|---|
| 1-[1-oxo-2-[4-(2-sulfobenzoyl)amino-1H-imidazol-1-yl]octyl-4-cis-(2-naphthoxy)-L-proline | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

| | Quantity (mg/capsule) |
|---|---|
| 1-[1-oxo-2-[4-(2-sulfobenzoyl)amino-1H-imidazol-1-yl]octyl-4-cis((4-methylene phosphonic acid)-phenoxy)-L-proline | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

| | Quantity (mg/capsule) |
|---|---|
| 1-[1-oxo-2-[4-(2-sulfobenzoyl)amino-1H-imidazol-1-yl]octyl-4-cis-(4-t-butyloxyphenoxy)-L-proline | 0.25 |
| ethanol | 29.75 |
| Propellant 22 (chlorodifluoromethane) | 70.00 |
| Total | 100.00 |

The active compound is mixed with ethanol. The mixture is added to a portion of the Propellant 22, cooled to $-30°$ C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| | Quantity (mg/capsule) |
|---|---|
| 1-[1-oxo-2-[4-(2-sulfobenzoyl)amino-1H-imidazol-1-yl]octyl-4-cis-(4-methylsulfonylphenoxy)-L-proline | 60 mg |
| starch | 45 mg |
| microcrystalline cellulose | 35 mg |
| polyvinylpyrrolidone (as 10% solution in water) | 4 mg |

-continued

| | Quantity (mg/capsule) |
|---|---|
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| | Quantity (mg/capsule) |
|---|---|
| 1-[1-oxo-2-[4-(2-sulfobenzoyl)amino-1H-imidazol-1-yl]octyl-4-cis-(5-benzofuranoxy)-L-proline | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

| | Quantity (mg/capsule) |
|---|---|
| 1-[1-oxo-2-[4-(2-sulfobenzoyl)amino-1H-imidazol-1-yl]octyl-4-cis-(5-benzothiophenoxy)-L-proline | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | Quantity (mg/capsule) |
|---|---|
| 1-[1-oxo-2-[4-(2-sulfobenzoyl)amino-1H-imidazol-1-yl]octyl-4-cis-(4- | 50 mg |

-continued

| | Quantity (mg/capsule) |
|---|---|
| carboxymethylphenoxy)-L-proline | |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | Quantity (mg/capsule) |
|---|---|
| 1-[1-oxo-2-[4-(2-sulfobenzoyl)amino-1H-imidazol-1-yl]octyl-4-cis-(4-hydroxyphenoxy)-L-proline | 250 mg |
| isotonic saline | 1000 mg |

The solution of the above ingredients is administered intravenously at a rate of 1 ml per minute to a subject in need of treatment.

We claim:

1. A process of preparing a substantially pure (R) enantiomer of the compound of the formula:

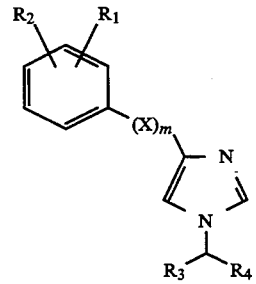

wherein:

$R_1$ is $CO_2H$, $SO_3H$, $PO_3H_2$, $CONHSO_2R_5$ or 5-tetrazolyl;

$R_2$ is H, —OH, —OCOCH$_3$, halo, $C_1$–$C_4$ alkyl, amino, acetamido, or $C_1$–$C_4$ alkoxy;

x is —(CH$_2$)$_m$NHCO—, —(CH$_2$)$_m$CONH—, —O—, —NH—, —CH$_2$—, —(CH$_2$)$_m$CO—, or —CO(CH$_2$)$_m$—;

$R_3$ is $C_4$–$C_9$ straight chain alkyl, $C_4$–$C_9$ straight chain trifluoroalkyl, $C_4$–$C_9$ straight chain alkenyl, or $C_4$–$C_9$ straight chain trifluoroalkenyl;

$R_4$ is —CONH($C_1$–$C_4$ alkyl), —CONH($C_1$–$C_4$ trifluoroalkyl), —CONH(hydroxy-$C_1$–$C_4$ alkyl),

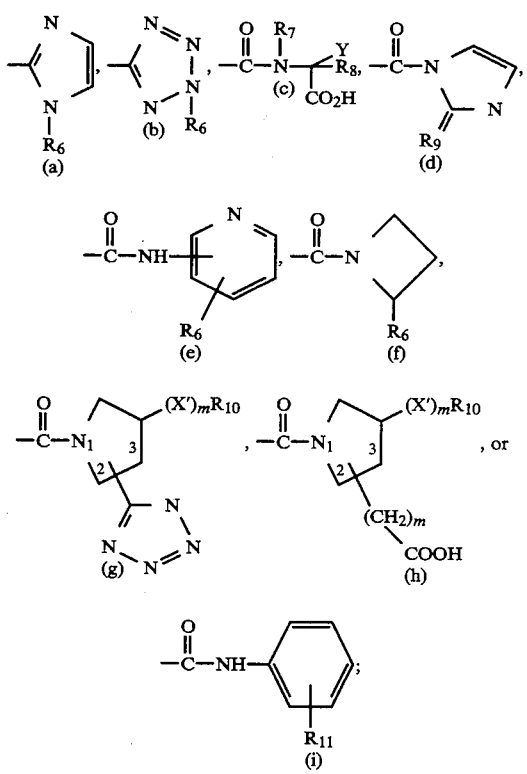

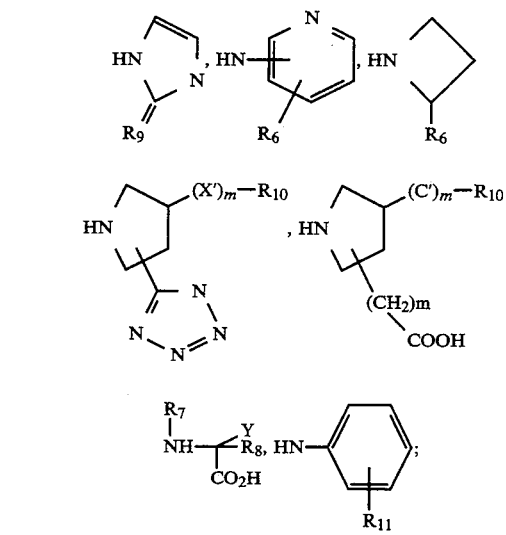

$R_5$ is phenyl, $C_1$–$C_4$ alkyl substituted phenyl, $C_1$–$C_5$ alkyl, or $C_1$–$C_5$ trifluoroalkyl;

$R_6$ is $(CH_2)_p R_1$, or $C_1$–$C_4$ alkyl;

$R_7$ is H or $CH_3$;

$R_8$ is H or $-(CH_2)_q R_{12}$;

$R_9$ is O or S;

$R_{10}$ is H, $-(CH_2)_p R_1$, $C_1$–$C_7$ alkyl, $C_1$–$C_7$ trifluoroalkyl, halo, substituted or unsubstituted phenyl, 3-pyridyl, 2-pyrimidyl, furanyl, oxazolyl, isoxazolyl, a substituted or unsubstituted fused bicyclic, a substituted or unsubstituted fused tricyclic, or when m is 0, 4,4-ethylenedioxy;

$R_{11}$ is H, OH, $C_1$–$C_4$ alkoxy, $CO_2H$, $SO_3H$, $PO_3H_2$, $CONHSO_2R_5$, or tetrazolyl;

$R_{12}$ is OH, $NH_2$, or $CO_2H$:

Y is a R group of a naturally occurring amino acid;

X' is $-O-$, $-(CH_2)_p-$, or $-S-$;

m is independently 0 or 1;

p is independently 0, 1, 2, 3 or 4; and q is 1, 2, 3, or 4:

providing that when $R_4$ is (g) or (h), and $R_{10}$ is not H, the carboxy of (h) or tetrazolyl of (g) is in position 2; and when $R_4$ is (g) or (h), m is 0, and $R_{10}$ is H, the carboxy of (g) or tetrazolyl of (h) is in position 2 or 3; comprising coupling a compound of the formula (XXI)

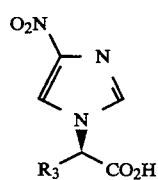

wherein $R_3$ is $C_4$–$C_9$ straight chain alkyl, $C_4$–$C_9$ straight chain trifluoroalkyl, $C_4$–$C_9$ straight chain alkenyl, or $C_4$–$C_9$ straight chain trifluoroalkenyl; to a compound of the formula:

wherein $R_6$ is $(CH_2)_p R_1$, or $C_1$–$C_4$ alkyl; $R_7$ is H or $CH_3$; $R_8$ is H or $-(CH_2)_q R_{12}$; $R_9$ is O or S; $R_{10}$ is H, $-(CH_2)_p R_1$, $C_1$–$C_7$ alkyl, $C_1$–$C_7$ trifluoroalkyl, halo, substituted or unsubstituted phenyl, 3-pyridyl, 2-pyrimidyl, furanyl, oxazolyl, isoxazolyl, a substituted or unsubstituted fused bicyclic, a substituted or unsubstituted fused tricyclic, or when m is 0, 4,4-ethylenedioxy; $R_{11}$ is H, OH, $C_1$–$C_4$ alkoxy, $CO_2H$, $SO_3H$, $PO_3H_2$, $CONHSO_2R_5$, or tetrazolyl; $R_{12}$ is OH, $NH_2$, or $CO_2H$; Y is a R group of a naturally occurring amino acid; providing that when $R_4$ is (g) or (h), and $R_{10}$ is not H, the carboxy of (h) or tetrazolyl of (g) is in position 2; and when $R_4$ is (g) or (h), m is 0, and $R_{10}$ is H, the carboxy of (g) or tetrazolyl of (h) is in position 2 or 3;

reducing the nitro of the compound of the formula (XXI) to produce an amino imidazole;

coupling the amino imidazole to a compound of the formula:

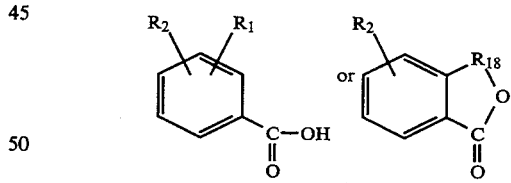

wherein $R_2$ is H, $-OH$, $-OCOCH_3$, $-$halo, $C_1$–$C_4$ alkyl, amino, acetamido, or $C_1$–$C_4$ alkoxy, $R_1$ is $CO_2H$, $SO_3H$, $PO_3H_2$, $CONHSO_2R_5$ or 5-tetrazolyl, $R_{18}$ is $SO_2$ or $C=O$.

2. The method of claim 1 wherein the amino imidazole is coupled to an anhydride of the formula

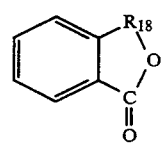

wherein $R_{18}$ is $SO_2$ or $C=O$.

3. The method of claim 2 wherein $R_{18}$ is $SO_2$.

4. The method of claim 3 to produce a compound of the formula:

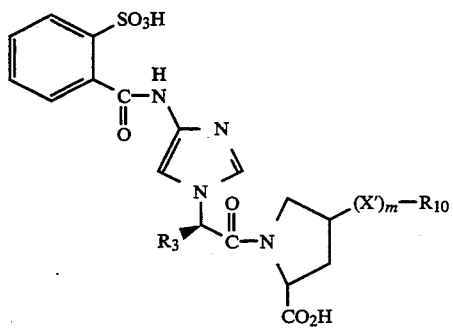

5. The method of claim 14 wherein X' is —O—, $R_{10}$ is a substituted phenyl of the formula:

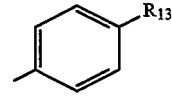

wherein $R_{13}$ is —$(CH_2)_pR_1$, —$O(CH_2)_pR_1$, —$SO_2NR_{14}R_{15}$, —$(CH_2)_pCONR_{14}R_{15}$, —$(CH_2)_pNR_{16}SO_2(C_1-C_4$ alkyl or $C_1-C_4$ trifluoroalkyl), or a heteroaryl selected from imidazole, triazolyl, tetrazolyl, thioazolyl, isoxazolyl, or oxazolyl, said heteroaryl being optionally substituted with —$(CH_2)_pR_1$; $R_{14}$ and $R_{15}$ are independently H, $C_1-C_4$ alkyl or taken together with nitrogen to which they are bonded constitute a heterocylic ring selected from the groups consisting of pyrrolidino or piperidino, said heterocylic ring being optionally substituted with —COOH; $R_{16}$ is H or $C_1-C_4$ alkyl.

6. The method of claim 5 wherein $R_{13}$ is —$(CH_2)_pR_1$; and $R_1$ is $CO_2H$ or $PO_3H_2$; and p is 1.

7. The method of claim 6 wherein the compound produced is cis-4-[4-(carboxymethyl)phenoxy]-1-[1-oxo-2(R)-[4-(2-sulfobenzyl)amino]-1H-imidazol-1-yl]octyl]-L-proline.

8. The method of claim 7 wherein the compound produced is cis-4-[((4-methylene phosphonic acid)-phenoxy]-1-[1-oxo-2(R)-[4-(2-sulfobenzyl)amino]-1H-imidazol-1-yl]octyl]-L-proline.

* * * * *

UNITED STATES PATENT AND TRADEMARK OFFICE
CERTIFICATE OF CORRECTION

PATENT NO. : 5,401,851
DATED : March 28, 1995
INVENTOR(S) : Boyd, et. al.

It is certified that error appears in the above-indentified patent and that said Letters Patent is hereby corrected as shown below:

Column 53, Line 26
5. The method of claim 4 wherein X' is -O-, $R_{10}$

Signed and Sealed this

Twenty-second Day of August, 1995

Attest:

BRUCE LEHMAN

Attesting Officer           Commissioner of Patents and Trademarks